(12) United States Patent
Olson et al.

(10) Patent No.: US 7,880,607 B2
(45) Date of Patent: Feb. 1, 2011

(54) INTELLIGENT RISK MANAGEMENT SYSTEM FOR FIRST RESPONDERS

(75) Inventors: William L. Olson, Palatine, IL (US); Magdi A. Mohamed, Schaumburg, IL (US)

(73) Assignee: Motorola, Inc., Schaumburg, IL (US)

( * ) Notice: Subject to any disclaimer, the term of this patent is extended or adjusted under 35 U.S.C. 154(b) by 672 days.

(21) Appl. No.: 11/611,321

(22) Filed: Dec. 15, 2006

(65) Prior Publication Data

US 2008/0146895 A1    Jun. 19, 2008

(51) Int. Cl.
  *G08B 19/00* (2006.01)
(52) U.S. Cl. ............... 340/521; 340/523; 340/573.1
(58) Field of Classification Search ............ 340/573.1, 340/573.5, 573.7, 505, 539.11, 539.12, 539.13, 340/539.26, 521, 523; 348/82; 382/159; 280/735; 600/511; 702/118; 705/2
  See application file for complete search history.

(56) References Cited

U.S. PATENT DOCUMENTS

| | | | |
|---|---|---|---|
| 4,438,504 A | | 3/1984 | Favin |
| 4,893,316 A | | 1/1990 | Jane et al. |
| 5,576,497 A | | 11/1996 | Vignos et al. |
| 5,754,681 A | * | 5/1998 | Watanabe et al. ............ 382/159 |
| 5,909,384 A | | 6/1999 | Tal et al. |
| 6,009,448 A | | 12/1999 | Jong et al. |
| 6,154,547 A | | 11/2000 | Whitecar |
| 6,606,993 B1 | * | 8/2003 | Wiesmann et al. ..... 128/204.23 |
| 6,633,327 B1 | * | 10/2003 | Williams et al. .............. 348/82 |
| 6,671,663 B1 | | 12/2003 | Hellums et al. |
| 6,907,284 B2 | * | 6/2005 | Hamilton et al. ............ 600/511 |
| 6,934,571 B2 | * | 8/2005 | Wiesmann et al. .......... 600/326 |
| 6,995,665 B2 | * | 2/2006 | Appelt et al. ............... 340/521 |
| 7,117,128 B2 | | 10/2006 | Mohamed et al. |
| 7,243,945 B2 | * | 7/2007 | Breed et al. ................. 280/735 |
| 7,245,216 B2 | * | 7/2007 | Burkley et al. ......... 340/539.13 |
| 7,313,502 B2 | * | 12/2007 | Schuster et al. ............. 702/188 |
| 7,342,502 B2 | * | 3/2008 | Harkins et al. ........... 340/573.1 |
| 7,613,758 B2 | | 11/2009 | Xiao et al. |
| 2002/0055857 A1 | * | 5/2002 | Mault ............................. 705/2 |
| 2002/0181615 A1 | | 12/2002 | Kuzminskiy et al. |
| 2004/0012433 A1 | | 1/2004 | Kim et al. |
| 2005/0927815 | | 12/2005 | Mohamed et al. |

(Continued)

FOREIGN PATENT DOCUMENTS

WO   WO 2005-119473 A2   12/2005

(Continued)

OTHER PUBLICATIONS

Corredoura, et al., "Low Level RF System Design for the PEP-LL B Factory," Stanford Publications, 1996, pp. 1-3.

(Continued)

*Primary Examiner*—Van T. Trieu

(57) ABSTRACT

A risk management system (100) for first responders (102) equips first responders with physiological and environmental sensors (104) in order to track the stress conditions and stress responses of the first responders. Data from the sensors is digitized and filtered and processed through a feature extraction system (202, 704) that may include noise filters, (710) derivative filters (706), integrators (708) and derived signal generators (712) that use stored data on first responders, before being fed into a pattern recognition system (402, 900) that assesses the risk state of the first responder. Data from multiple first responders in a team can be aggregated to obtain team risk assessments.

38 Claims, 16 Drawing Sheets

U.S. PATENT DOCUMENTS

2006/0195499 A1   8/2006   Xiao et al.
2008/0001735 A1*  1/2008   Tran .................. 340/539.22

FOREIGN PATENT DOCUMENTS

WO   WO 2006-088569 A2   8/2006

OTHER PUBLICATIONS

Diamond, "Calibration of an Audio Frequency Noise Generator," IEEE Transactions on Audio and Electroacoustics, vol. AU-14, No. 2, Jun. 1966, pp. 96-100.

Dulger, et al., A 1.3-V 5-mW Fully Integrated Tunable Bandpass Filter at 2.1 GHz in 0.35-µm CMOS, IEEE Journal of Solid-State Circuits, vol. 38, No. 6, Jun. 2003, pp. 918-928.

Grabisch, "Fuzzy Integrals as a Generalized Class of Order Filters," Proceedings of SPIE, vol. 2315, 1994, pp. 128-136.

Grossert, et al., "A New Approach to Fuzzy Morphology Based on Fuzzy Integral and Its Application in Image Processing," IEEE Proceedings ICPR '96, 1996, pp. 625-630.

Hocaoglu, et al., Nonlinear Filters for Target Detection in LADAR Range Images, IEEE Journal, Sep. 1997, pp. 177-182.

Mohamed, et al., "Q-Measures: an Efficient Extension of the Sugeno $\lambda$,-Measure," IEEE Transactions on Fuzzy Systems, vol. 11, No. 3, Jun. 2003, pp. 419-426.

Shi, et al., Fuzzy Integral Filters: Properties and Parallel Implementation, Real Time Imaging, Acedemic Press Limited, vol. 4, No. 4, Aug. 1998, pp. 233-241.

* cited by examiner commander's data terminal

2-D CROSS SECTION OF PATTERN RECOGNITION
FEATURE VECTOR SPACE

TRAINING REGIMEN

INTELLIGENT RISK MANAGEMENT SYSTEM FOR FIRST RESPONDERS

FIELD OF THE INVENTION

The present invention relates generally to real-time personnel risk management.

BACKGROUND

The events of Sep. 11, 2001, brought to the fore concern for the safety of first responders such as firefighters. Firefighters and other first responders are often tasked with perilous duties. Contrary to widespread conception most firefighter fatalities do not die instantly when a building collapses or by being engulfed in flames. In fact, many firefighters succumb to heart failure brought about by the almost pathological combination of conditions of firefighting. Firefighters must work in heavy gear which although designed to protect them from the heat of fires also unfortunately serves to trap their own body heat which can lead to dehydration and accelerate physical exhaustion. In combination with the heavy gear the proximity of the fire causes further heating. At the same time, they are called on to perform strenuous tasks such as deploying heavy hoses, breaking through doors and walls and working hose lines under unpredictable emergency conditions. Moreover, in some cases they are subject to fumes and/or particulates in the air or must make due with breathing through Self Contained Breathing Apparatus (SCBA). Although firefighters are well known for their physical fitness, nonetheless the combination of conditions tends to put them at risk for cardiac arrest or injury due to mistakes made more likely due to fatigue or exhaustion. It would be desirable to provide an automated system for managing the stress levels and conditions of first responders with the aim of reducing first responder injuries and fatalities.

BRIEF DESCRIPTION OF THE FIGURES

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

Figure 1:
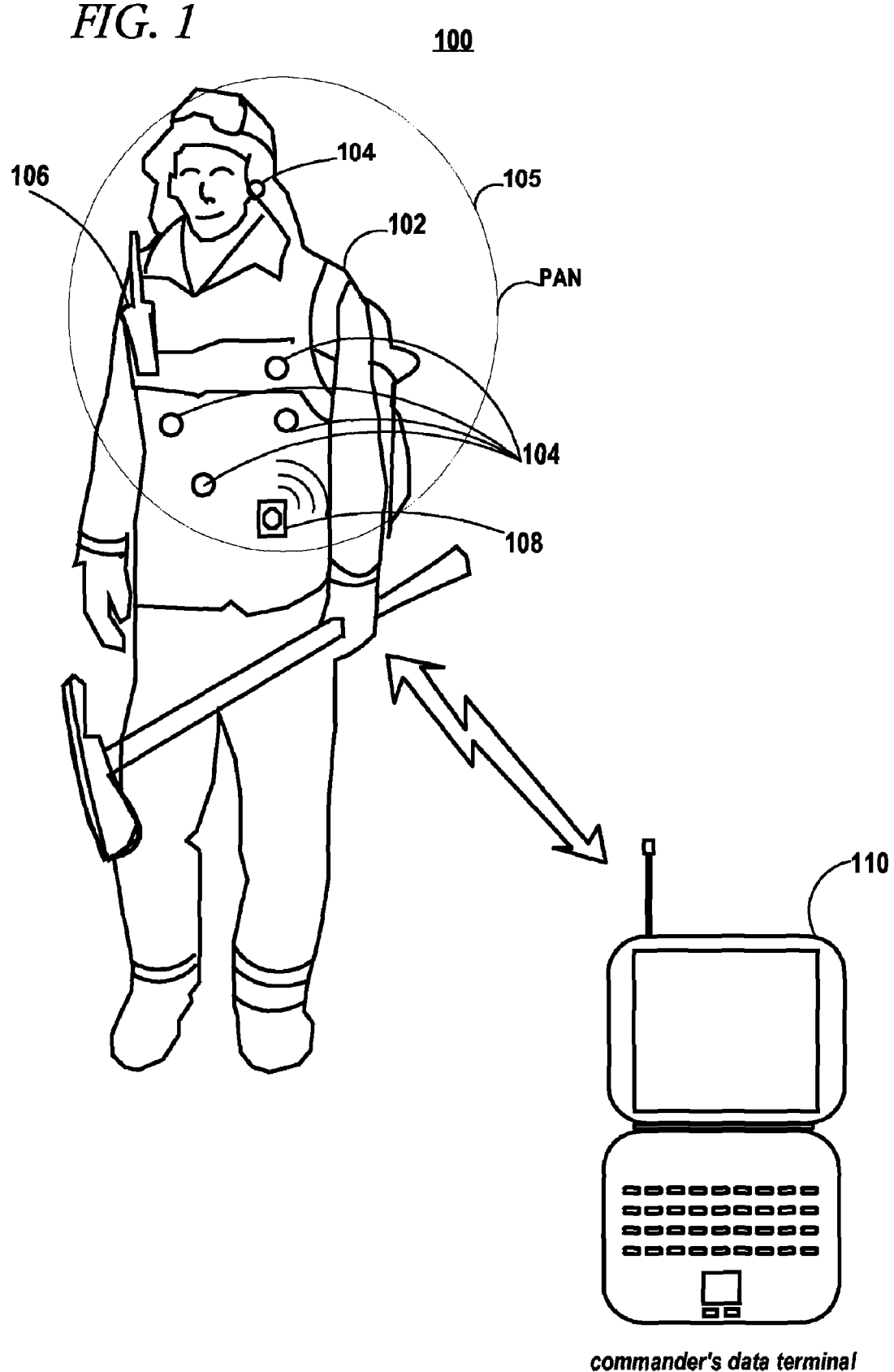
FIG. 1 is a pictorial illustration of an intelligent risk management system for first responders.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION

Before describing in detail embodiments that are in accordance with the present invention, it should be observed that the embodiments reside primarily in combinations of method steps and apparatus components related to first responder risk management. Accordingly, the apparatus components and method steps have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

In this document, relational terms such as first and second, top and bottom, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

It will be appreciated that embodiments of the invention described herein may be comprised of one or more conventional processors and unique stored program instructions that control the one or more processors to implement, in conjunction with certain non-processor circuits, some, most, or all of the functions of first responder risk management described herein. The non-processor circuits may include, but are not limited to, a radio receiver, a radio transmitter, signal drivers, clock circuits, power source circuits, and user input devices. As such, these functions may be interpreted as steps of a method to perform first responder risk management. Alternatively, some or all functions could be implemented by a state machine that has no stored program instructions, or in one or more Application Specific Integrated Circuits (ASICs) or Field Programmable Gate Arrays (FPGAs), in which each function or some combinations of certain of the functions are implemented as custom logic. Of course, a combination of these approaches could be used. Thus, methods and means for these functions have been described herein. Further, it is expected that one of ordinary skill, notwithstanding possibly significant effort and many design choices motivated by, for example, available time, current technology, and economic considerations, when guided by the concepts and principles disclosed herein will be readily capable of generating such software instructions and programs and Integrated Circuits (ICs) with minimal experimentation.

FIG. 1 is a pictorial illustration of an intelligent risk management system for first responders 100. A first responder 102 is equipped with several sensors 104. The sensors 104 can include environmental sensors used to sense conditions that effect the environmental stress level on the first responder (e.g., clothing temperature sensors, smoke detectors, carbon monoxide sensors) as well as physiological sensors (e.g., body temperature sensors, heart rate sensors, pulse oximeter sensors, and/or blood pressure sensors) used to sense the stress level induced by the environment and the work load of the first responder 102. The sensors 104 can be connected by a Personal Area Network (PAN) 105 or by signal conduits (e.g., twisted pairs, fiber optics) to a portable radio/computer 106 that is equipped with signal processing circuits and is capable of data communication (e.g., Wireless Access Protocol (WAP)). A handheld data terminal such as the HDT600, made by the assignee of the instant invention Motorola of Schaumburg, Ill. can be used as the portable radio/computer 106. The sensors 104 can be attached to the first responder's 102 clothing, shoes, or worn on the body using various straps (e.g., a chest strap) or other devices (e.g., clips).

An alert 108 which can be audible, visual (e.g., flashing light), and/or tactile (e.g., vibrator) is also part of the first responder's 102 gear. The alert 108 can be used to alert the first responder 102 that he or she is at risk for injury brought about by cardiovascular and/or environmental stress.

The portable radio/computer 106 is connected by a wireless channel to a commander's data terminal 110. The commander's data terminal 110 can take the form of a laptop computer equipped with a radio. A model ML900 mobile laptop made by Motorola can be used as the commander's data terminal 110.

Signal processing software and circuits that are used to determine a level of risk for the first responder 102 based on data from the sensors 104 and other information can be housed in the first responder's portable radio/computer 106 or in the commanders data terminal 110 or partly in both.

Figure 2:
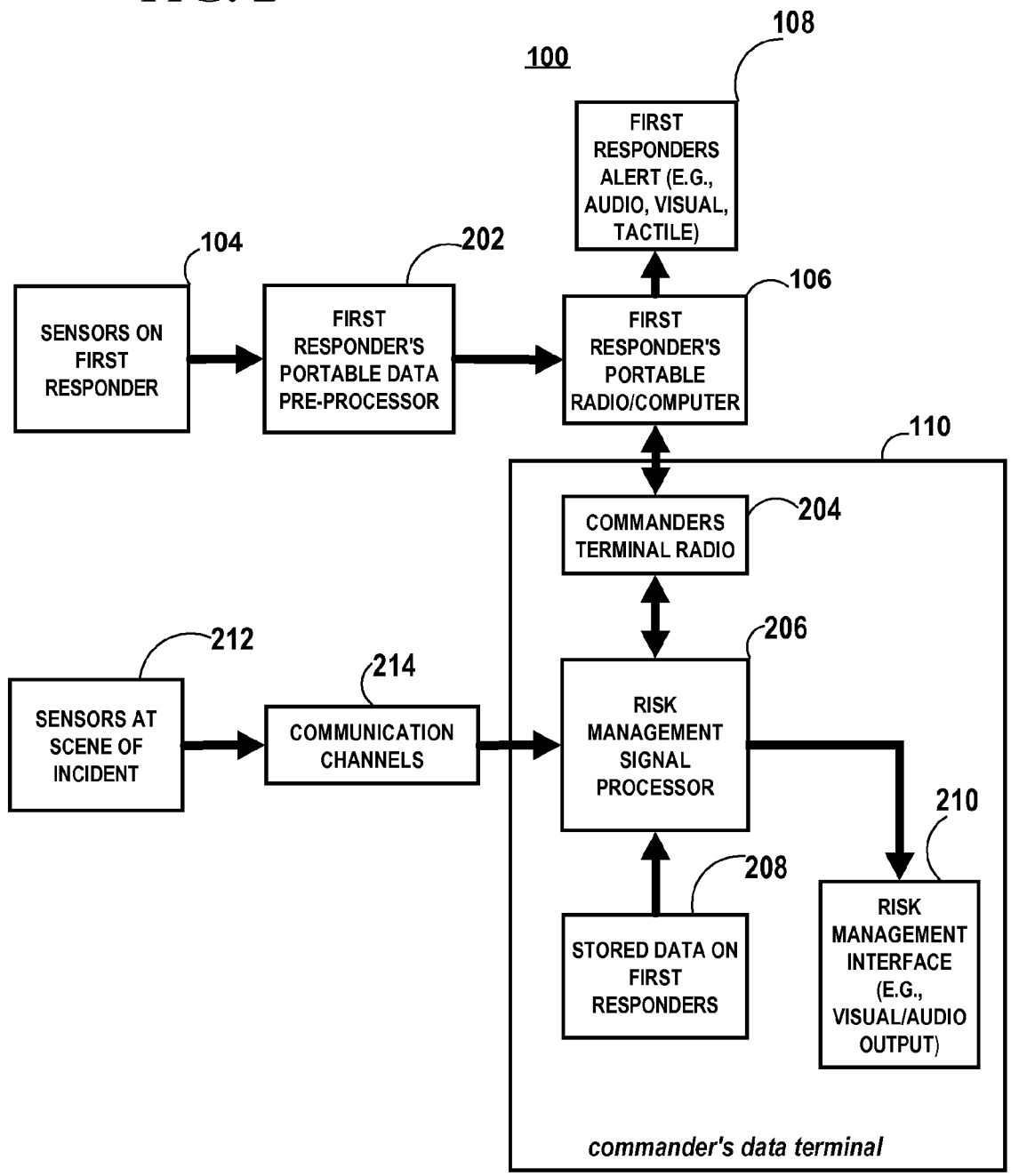
FIG. 2 is a block diagram of the intelligent risk management system for first responders shown in FIG. 1 according to an embodiment of the invention.

FIG. 2 is a block diagram of the intelligent risk management system for first responders 100 shown in FIG. 1 according to an embodiment of the invention. As shown in FIG. 2 the sensors 104 are coupled to a set of first responder's portable data pre-processors 202. The data pre-processor 202 can be housed in one or more separate electronic boxes carried by the first responder, can be incorporated into the portable radio/computer 106 and/or parts of the data pre-processor 202 can be built into the sensors 104. The sensors 104 are coupled through the data pre-processors 202 and the first responder's portable radio computer 106 to a commander's terminal radio 204. The alert 108 is coupled to the first responder's portable radio/computer 106, so that the alert 108 can be driven by a signal received from the commander's terminal radio 204. The alert 108 can also be driven by a signal generated by the first responder's portable radio/computer 106 acting autonomously.

In addition to the commander's terminal radio 204 the commander's data terminal 110 includes a risk management signal processor 206, stored data on first responders 208 and a risk management interface 210 (e.g., Graphical User Interface, GUI displayed on a display of the commander's data terminal 110). The risk management signal processor 206 is coupled to the other parts 204, 208, 210 of the commander's data terminal 110. Optionally sensors at the scene of an incident 212 (e.g., smoke detectors, carbon monoxide sensor) are coupled to the risk management signal processor 206 through other communication channels 214 (e.g., wireless communication channels). The risk management signal processor 206 can be implemented in hardware, software or a combination of the two. The risk management signal 206 processor processes information received from the first responder's sensors 104, the stored data on the first responder 208 and optionally information received from sensors at the scene of the incident 212 in order to determine the level of risk to the first responder. An indication of the level of risk is output through the risk management interface 210, and communicated back to the first responder's portable radio/computer 106 which then selectively activates the alert 108 based on the indication of the level of risk.

Figure 3:
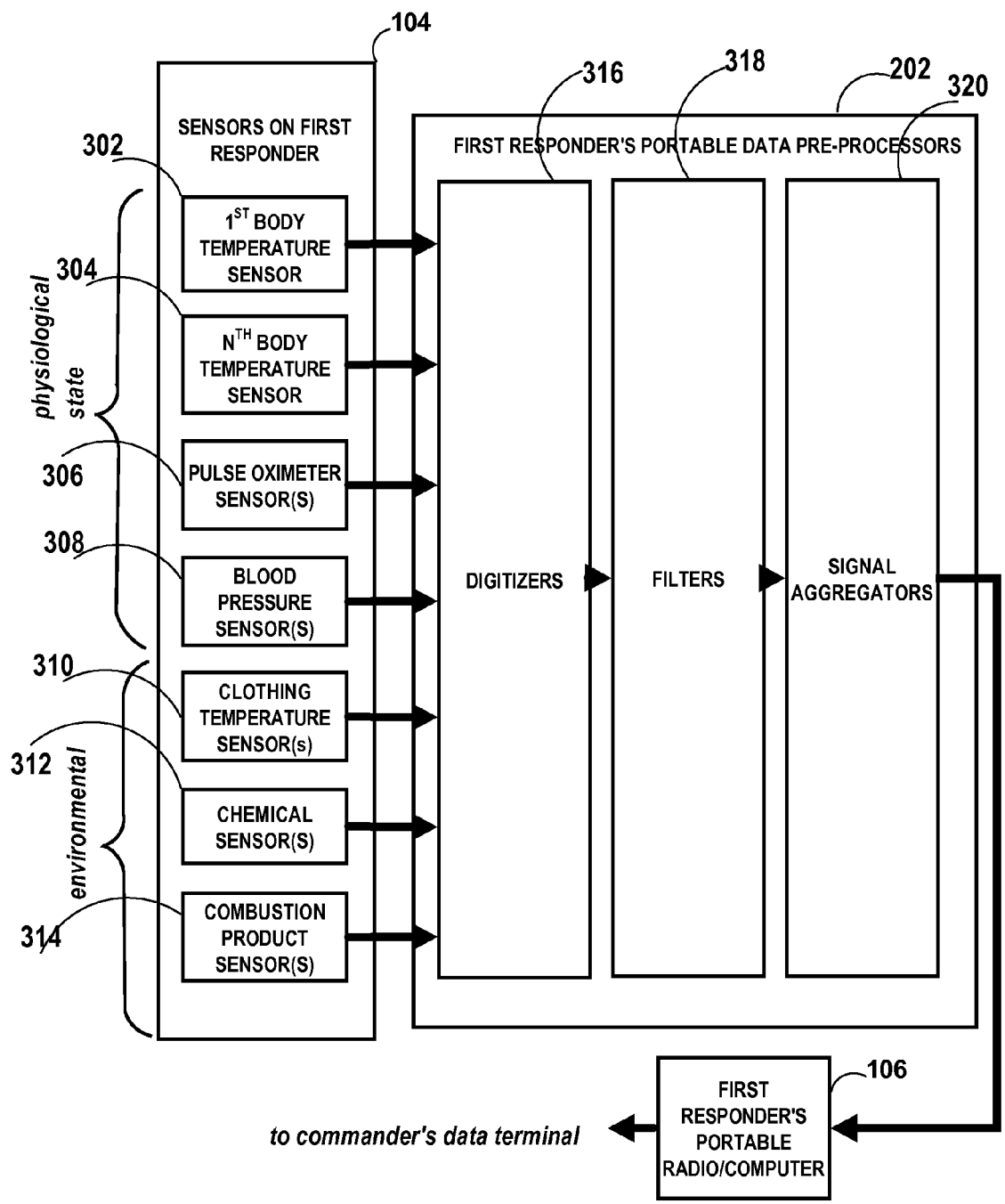
FIG. 3 is a block diagram of parts of the intelligent risk management system for first responders that are carried with the first responder according to an embodiment of the invention.

FIG. 3 is a block diagram of parts of the intelligent risk management system for first responders 100 that are carried with the first responder 102 according to an embodiment of the invention. As shown in FIG. 3 the sensors 104 that are carried with the first responder 102 (e.g., attached to the first responder's clothing, shoes, or body) include a plurality of physiological state sensors including a first body temperature sensor 302, an $N^{TH}$ body temperature sensor 304, one or more pulse oximeter sensors 306 and one or more blood pressure sensors 308. The sensors 104 that are carried with the first responder 102 also include a plurality of environmental sensors including one or more external clothing temperature sensors 310 (attached at or near the outside of the first responders clothing, so as to register ambient temperature), one or more chemical sensors 312 and one or more combustion product (e.g., carbon monoxide) sensors 314. The aforementioned sensors 302-314 are coupled through a set of digitizers 316, to a set of digital domain filters 318.

The set of digital domain filters 318 serve to reduce noise in signal received from the sensors 104. The set of digital domain filters 318 can include Finite Impulse Response (FIR) filters, Infinite Impulse Response (IIR) filters and/or filters specialized for specific sensors. The set of digital domain filters can also include Q-filters which are covered in U.S. Pat. No. 7,117,128 to Magdi Mohamed et al. or fast Q-filters which are covered in co-pending patent application Ser. No. 11/554,689 by Magdi Mohamed et al.

A Q-filter can be defined by the following sequence of equations:

$$e = r_{min} + C \qquad \text{EQU. 1}$$

where, e is a filtered signal, $r_{min}$ is a minimum of an ordered sequence of thresholds to which the input signal $S_j$ is compared. The ordered sequence of thresholds is represented as: $r_o < r_1 < \ldots < r_{m-1}$. Note that $r_{min} = r_o <= S_j <= r_{m-1} = r_{max}$. The input signal is bounded between minimum threshold $r_{min}$ and maximum threshold $r_{max}$. If necessary, pre-amplification or attenuation is used to scale the signal appropriately. Furthermore:

$$C = \sum_{i=1}^{m-1} q_i \frac{r_{max} - r_{min}}{m-1} = \frac{r_{max} - r_{min}}{m-1} \sum_{i=1}^{m-1} q_i \qquad \text{EQU. 2}$$

where $$q_i = \begin{cases} \dfrac{\prod_{j=1}^{n}(1+\lambda_f h_{ij} f_j) - 1}{F}, & \lambda_f \geq -1, \lambda_f \neq 0 \\ \dfrac{\sum_{j=1}^{n} h_{ij} f_j}{F}, & \lambda_f = 0 \end{cases} \qquad \text{EQU. 3}$$

where $\lambda_f >= -1$ is a filter defining parameter; and $$F = \begin{cases} \prod_{j=1}^{n}(1+\lambda_f f_j) - 1, & \lambda_f \geq -1, \lambda_f \neq 0 \\ \sum_{j=1}^{n} f_j, & \lambda_f = 0 \end{cases} \qquad \text{EQU. 4}$$

where, $f_j$ are a sequence of filter defining parameters in the range [0,1], and $h_{ij}=1$ for $S_j >= r_i$ and otherwise $h_{ij}=0$.

Generally the thresholds $r_i$ will be evenly spaced, although unevenly spaced thresholds may be used as well. Once the spacing of the thresholds has been fixed, the values of the filter nonlinearity control parameter λ and of the filter defining parameters $f_j$ remain to be fixed in order to fully define a Q-filter. The parameters λ and $f_j$ are suitably determined by an optimization procedure that seeks to match the output of the filter to a model desired output.

A fast Q-filter can be defined by the following set of equations:

$$e = \frac{1}{\Psi_1} \sum_{i=1}^{N} S_{index(i)}(\Psi_i - \Psi_{i-1}) \qquad \text{EQU. 5}$$

where, $\Psi_i = F(\text{Index}(i)) + \Psi_{i+1} + \lambda_f F(\text{Index}(i))\Psi_{i+1}, i = 1, \ldots, N$, $\Psi_{N+1} = 0$.

N is a number of signal samples in a sample window

Index(i) is an $i^{TH}$ element of a permutation array that describes a sorting of the N signal samples in the sample window;

$[f_1, f_2, f_3 \ldots f_j \ldots f_N]$ is a predetermined vector of filter defining parameters $f_j \in [0,1]$ for all $j=1, \ldots, N$ $\lambda_f$ is a filter nonlinearity control parameter that is greater than or equal to −1.

The filter defining parameters of the Q-filter and the fast Q-filter can be determined by optimization. The optimization is performed using training data that includes input data, and associated ideal output data. During optimization, the difference between the actual output of the Q-filter and the ideal output data is monitored while the values of λ and $f_j$ are adjusted in order to minimize the difference. A variety of optimization techniques, including but not limited to, methods that use simulated annealing, gradient information and direct-search methods can be used to optimize λ and $f_j$.

Alternatively, in lieu of digitizing the signals from the sensors 104 prior to filtering, some or all filtering can be performed in the analog domain. The filters 318 are coupled to a set of signal aggregators 320 to which filtered signals are supplied. Each aggregator combines filtered signals from multiple sensors. Signals from like (redundant) sensors can be aggregated, for example digitized signals from all of the body temperature sensors 302-304 can be aggregated. Optionally signals from dissimilar sensors which nonetheless relate to a common underlying state can be aggregated as well.

Alternatively, a microphone can be used to detect the first responder's heart beat. U.S. patent application Ser. No. 11/157,640 filed on June 2005, titled "Method for detecting heart rate and system thereof", by Hong et al., describes a system that uses dual Q-filters to extract a heart beat signal from a microphone signal.

Each aggregator can combine signals by averaging, generalized mean, MIN function, MAX function or fuzzy infinite logic aggregator for example. Co-pending patent application Ser. No. 11/554,674 entitled "Method and Apparatus for Nonlinear Signal and Data Aggregation" by Magdi Mohamed et al., filed Oct. 30, 2006 teaches a new type of aggregator that is configurable to perform a range of infinite logic aggregation operations ranging from a fuzzy intersection operation through an averaging operation to a fuzzy union operation. The operation of this aggregator can be described by the following equation:

$$A_{\lambda_A}(a_1, \ldots, a_n) = \begin{cases} \dfrac{\prod_{i=1}^{n}(1+\lambda_A a_i) - 1}{\prod_{i=1}^{n}(1+\lambda_A) - 1} & \lambda_A \geq -1, \lambda_A \neq 0 \\ \dfrac{1}{n}\sum_{i=1}^{n} a_i & \lambda_A = 0 \end{cases} \qquad \text{EQU. 6}$$

where, $\lambda_A >= -1$ is a magnitude of a connective control parameter;

$a_k \in [0,1]$ is a value of a $k^{th}$ input signal;

n>1 is an integer number of input signals; and $A_{\lambda_A}(a_1, \ldots, a_n) \in [0,1]$ is the output signal magnitude.

The number of inputs n is varied as needed. The inputs $a_k$ are suitably in the range from zero to one and the control parameter $\lambda_A$ is suitably greater than or equal to minus one. For such ranges of the inputs $a_k$ and control signal $\lambda_A$ the output $A_{\lambda_A}(a_1, \ldots, a_n)$ is also in the range zero to one. When the control parameter $\lambda_A$ is set to a high value e.g., one-hundred, the aggregator performs a fuzzy intersection-like connective (conjunctive) function. When the control parameter λ is set to minus one, the aggregator performs a fuzzy union-like connective (disjunctive) function and when the control parameter is set to zero the aggregator performs a linear averaging function. Not necessarily all of the signals from the sensors are subject to aggregation. Moreover, alternatively signal aggregation is not used in the pre-processors 202. If aggregation is used, output of the signal aggregators is coupled to the first responder's portable radio/computer 106 which sends signals output by the aggregators to the commander's data terminal 110.

Figure 4:
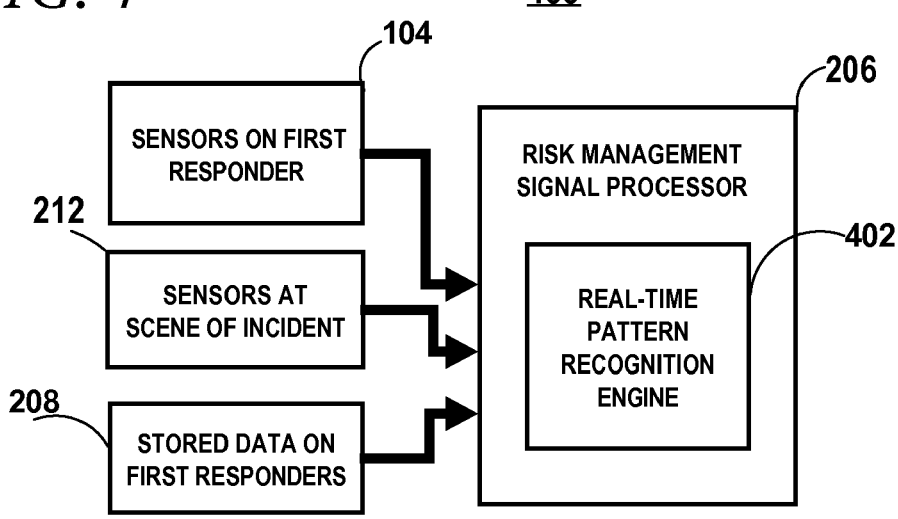
FIG. 4 is a block diagram of part of the intelligent risk management system for first responders shown in FIGS. 1-2 including a risk management signal processor.

FIG. 4 is a block diagram of part of the intelligent risk management system for first responders 100 shown in FIGS. 1-2. As shown in FIG. 4 the risk management signal processor 206 includes a real-time pattern recognition engine 402. Any of a variety of known and yet to be developed pattern recognition engines may be used. Examples of pattern recognition approaches that may be used include: Linear Discriminants, Quadratic Discriminants, Gaussian Mixtures, K-Nearest Neighbor, Hidden Markov Models, Support Vector Machines, Artificial Neural Networks, Tree Based Classifiers, Expert Systems, or Fuzzy Logic methods. Newly developed pattern recognition engine are taught in co-pending patent applications: Ser. No. 11/554,724 entitled "Artificial Neural Network With Adaptable Infinite-Logic Nodes", filed Oct. 31, 2006 by Weimin Xiao et al.; and Ser. No. 11/554,643 entitled "System for Pattern Recognition with Q-Metrics"; filed Oct. 30, 2006 by Magdi Mohamed et al. As shown in FIG. 4 the risk management signal processor 206 receives signals from the sensors on the first responder 104, and sensors at the scene of the incident 212. In general, a pattern recognition engine takes a feature vector as input an outputs an identification of a class represent by the feature vector. In the present application the feature vector is a real-time signal vector and the output of the pattern recognition engine represents a probable state of each first responder (e.g., "low risk", "moderate risk", "high risk").

Figure 5:
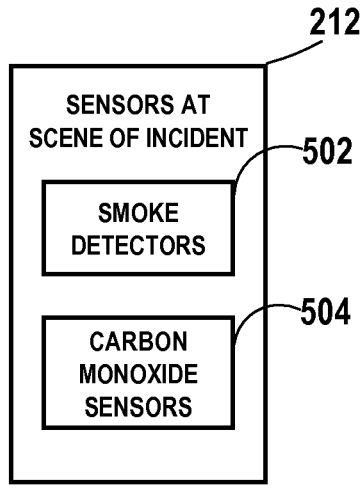
FIG. 5 is a block diagram of part of the risk management system shown in FIGS. 1-2 including sensors at a scene of an incident that provide input to the risk management signal processor shown in FIG. 4 according to an embodiment of the invention.

FIG. 5 is a block diagram of part of the risk management system shown in FIGS. 1-2 including sensors at a scene of an incident that provide input to the risk management signal processor shown in FIG. 4 according to an embodiment of the invention. Examples of sensors at the scene of the incident include smoke detectors 502 and carbon monoxide sensors 504. The sensors at the scene of the incident 502, 504 can be part of built-in infrastructure or autonomous wireless devices that are thrown, dropped or propelled into the scene of the incident by the first responder 102 or another.

Figure 6:
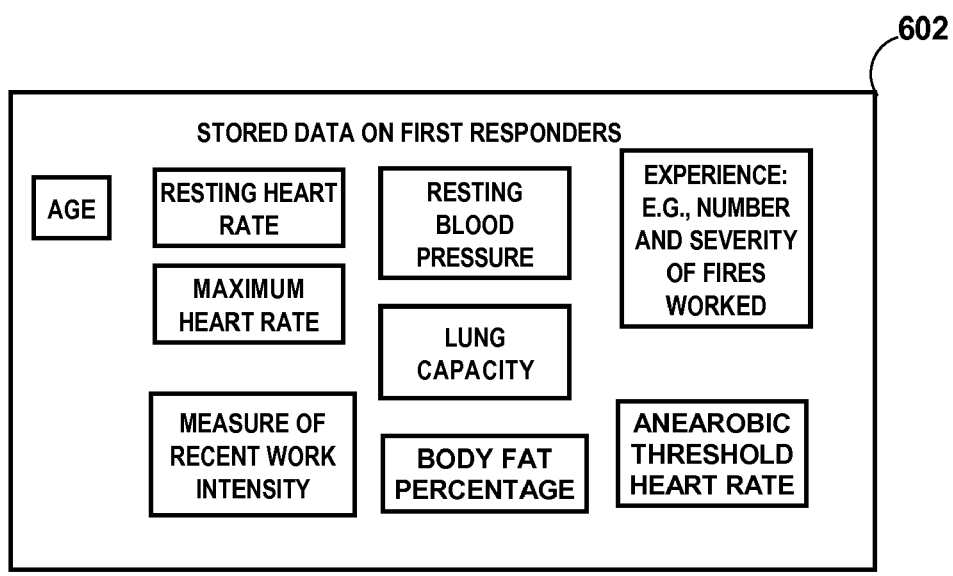
FIG. 6 is block diagram illustrating data on first responders that is used in the risk management signal processor shown in FIG. 4 according to an embodiment of the invention.

FIG. 6 is block diagram illustrating data 602 on first responders that is stored in memory and used by the risk management signal processor shown in FIG. 4 according to an embodiment of the invention. As shown in FIG. 6, the data can include the age of each first responder, the resting heart rate of each first responder, the maximum heart rate or each first responder (measured or calculated), the anaerobic threshold heart rate, the percent body fat, the resting blood pressure of each first responder, data on the experience of each first responder, and a measure of recent work intensity. The resting, maximum and anaerobic threshold heart rates are useful in assessing the stress level of each first responder based on the first responder's real-time heart rate data. Similarly, the resting blood pressure is useful in combination with actual real-time blood pressure data. The resting heart rate, resting blood pressure and lung capacity are useful, independently (e.g., as separate feature vector components) as measures of the fitness of each first responder. The data on the experience of each first responder can take the form of a single metric, for example and an intensity weighted sum of all calls worked by the first responder. Calls can be assigned weights (e.g., on a scale of one to ten) based on the level of emergency. The measure of recent work intensity is used to assess a possible level of fatigue and need for recovery before further exertion. The measure of recent work intensity can be based on heart rate. For example, the measure of recent work intensity can be an integral of heart beat above a predetermined threshold (e.g., resting heartbeat, anaerobic threshold heartbeat or a learned heart beat threshold) during calls during the last predetermined number of days (e.g. 10 days). The integrand can be weighted by a persistence function that gives greater weight to exertion during more recent calls.

Figure 7:
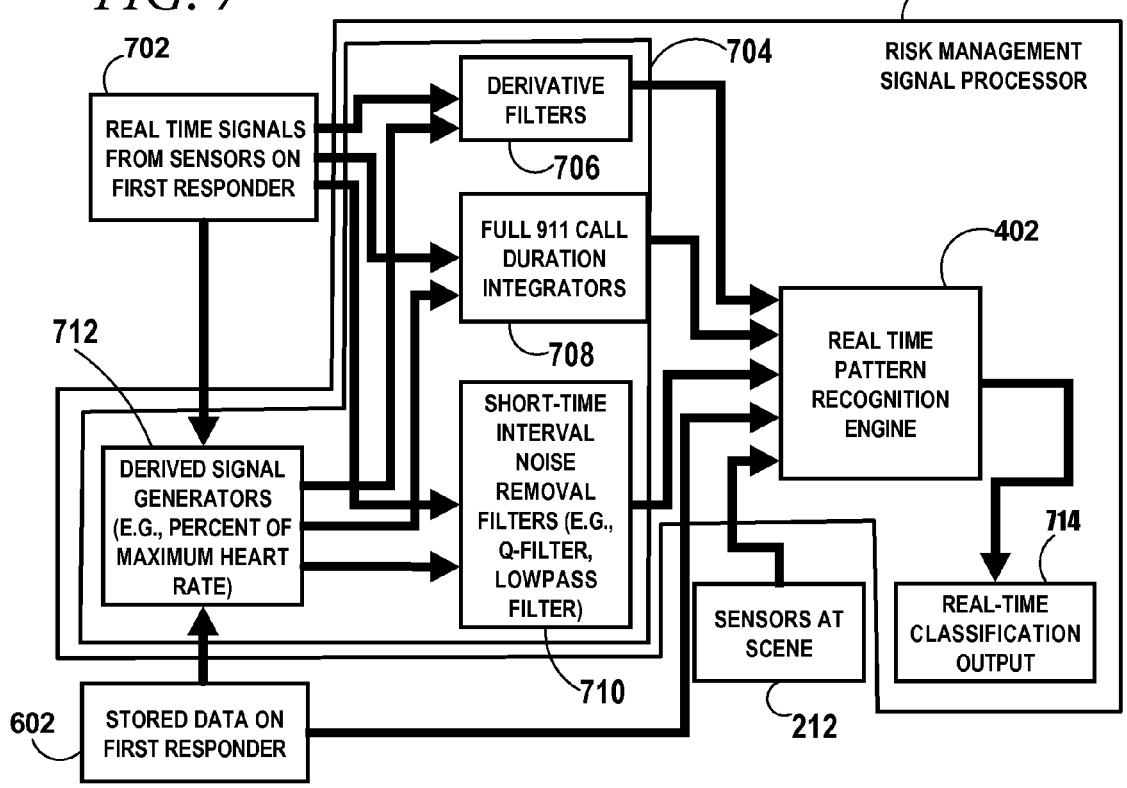
FIG. 7 is a block diagram showing details of the risk management signal processor shown in FIG. 4 according to an embodiment of the invention.

FIG. 7 is a block diagram showing details of the risk management signal processor shown in FIG. 4 according to an embodiment of the invention. Real-time signals from the sensors on the first responders 702 (which are received from the sensors on the first responders 104 through the first responder portable data pre-processor 202 and the first responder's portable radio/computer 106) are input into a feature vector extraction system 704. The feature vector extraction system 704 shown in FIG. 7 is just one example architecture, and it will be apparent to one skilled in the art that many variations on the feature vector extraction system are possible. As shown in FIG. 7 the feature vector extraction system 704 includes a set of derivative filters 706, a set of full call integrators 708, and a set of short time interval noise removal filters 710. The signal aggregators 320 of the first responder's portable data pre-processor 202 can also be considered part of a broader feature vector extraction system. All or subsets of the real-time signals from the first responder 702 can be coupled into the derivative filters 706, integrators 708 and noise removal filters 710. The derivative filters 706 serve to detect increasing danger in the environmental conditions (e.g., increasing smoke, or temperature) and increasing stress on the first responder as indicated, for example by a rapidly increasing heart rate. The integrators 708 are used to deduce the accumulated physiological and environmentally induced stress and during a 911 call. Alternatively, the integration period can be less that the full call (e.g. past 10 minutes). The integration period can be learned in training. Furthermore, the integrand of the integration can be weighted by a persistence function (backward decay) in order to weight more recent sensors readings more heavily. The noise removal filters 710 provide accurate estimates of instantaneous signal levels. Conventional low pass filters or Q-filters or fast Q-filters may be used as the noise removal filters. Alternatively, to what is shown in FIG. 7, input to the derivative filters 706 and the integrators 708 can be processed through the noise removal filters 710.

The stored data on the first responders 602 and the real-time signals from the sensors on the first responders 702 are coupled to a set of derived signal generators 712. One example of a derived signal is obtained by dividing a real-time pulse signal from the pulse oximeter(s) 306 by a maximum heart rate for the first responder that is stored or calculated based on stored age. Another example of a derived signal is obtained by thresholding the real-time pulse rate signal at an anaerobic threshold that is stored or calculated based on age. The thresholded output signal would be active when the first responder has a heartbeat above his or her anaerobic threshold and zero otherwise. Alternatively, the first responder's heartbeat can be thresholded at the first responder's resting heart beat. Derived signal generated by the derived signal generators 712 are also, at least selectively, coupled to the derivative filters 706, integrators 708 and noise removal filters 710. By way of example a first responders heart beat signal thresholded at the first responders anaerobic threshold (or alternatively a learned threshold) and integrated over the duration of an emergency call should give a good indication of how close to exhaustion the first responder is.

The output of the derivative filters 706, integrators 708 and noise removal filters 710 are coupled to feature vector inputs (signal vector inputs) of the real-time pattern recognition engine 402. Some or all of the data from sensors at the scene 212 and stored data on the first responders 602 can also be coupled to feature vector inputs of the real-time pattern recognition engine 402. The task of the real-time pattern recognition engine 402 is to determine a level of risk based on the input feature vector. An indication of the level of risk (e.g., "low risk", "moderate risk", "high risk") is output at a real-time classification output 714.

Figure 8:
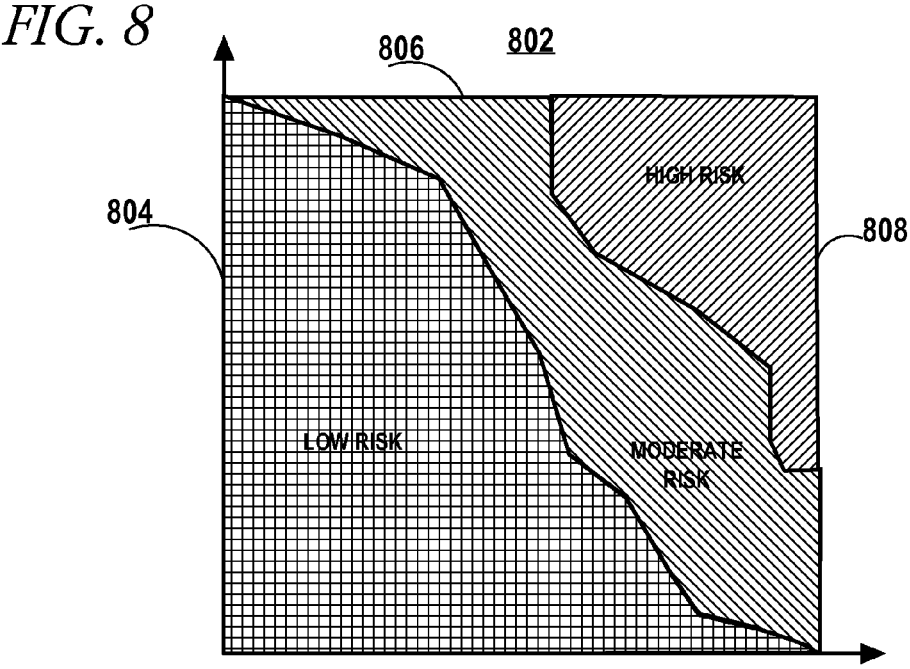
FIG. 8 is a schematic of a 2-D cross section of a pattern recognition feature vector space that is mapped by a pattern recognition engine that is part of the risk management signal processor shown in FIG. 7.

FIG. 8 is a schematic of a 2-D cross section of a pattern recognition feature vector space 802 that is mapped by the pattern recognition engine 402 that is part of the risk management signal processor 206 shown in FIG. 7. As shown in FIG. 8 the feature vector space 802 is divided into a "low risk" region 804, a "medium risk" region 806 and a "high risk" region 808. Depending on the type of pattern recognition engine that is used, the decision boundaries between the regions 804, 806, 808 may or may not be explicitly determined. In any case, the pattern recognition engine will classify the input feature vectors as corresponding to one of the conditions, e.g., "low risk", "medium risk" or "high risk". Typically pattern recognition systems are trained using labeled data. Alternatively, at least an initial configuration of the pattern recognition engine 402 can be established using hand selected values.

If based on experience with a certain feature vector extraction design, "medium risk" and "high risk" labeled feature vectors are found not to be well separated by linear or non-linear methods, then both can be subsumed into a single category that is distinguished from "low risk".

Figure 9:
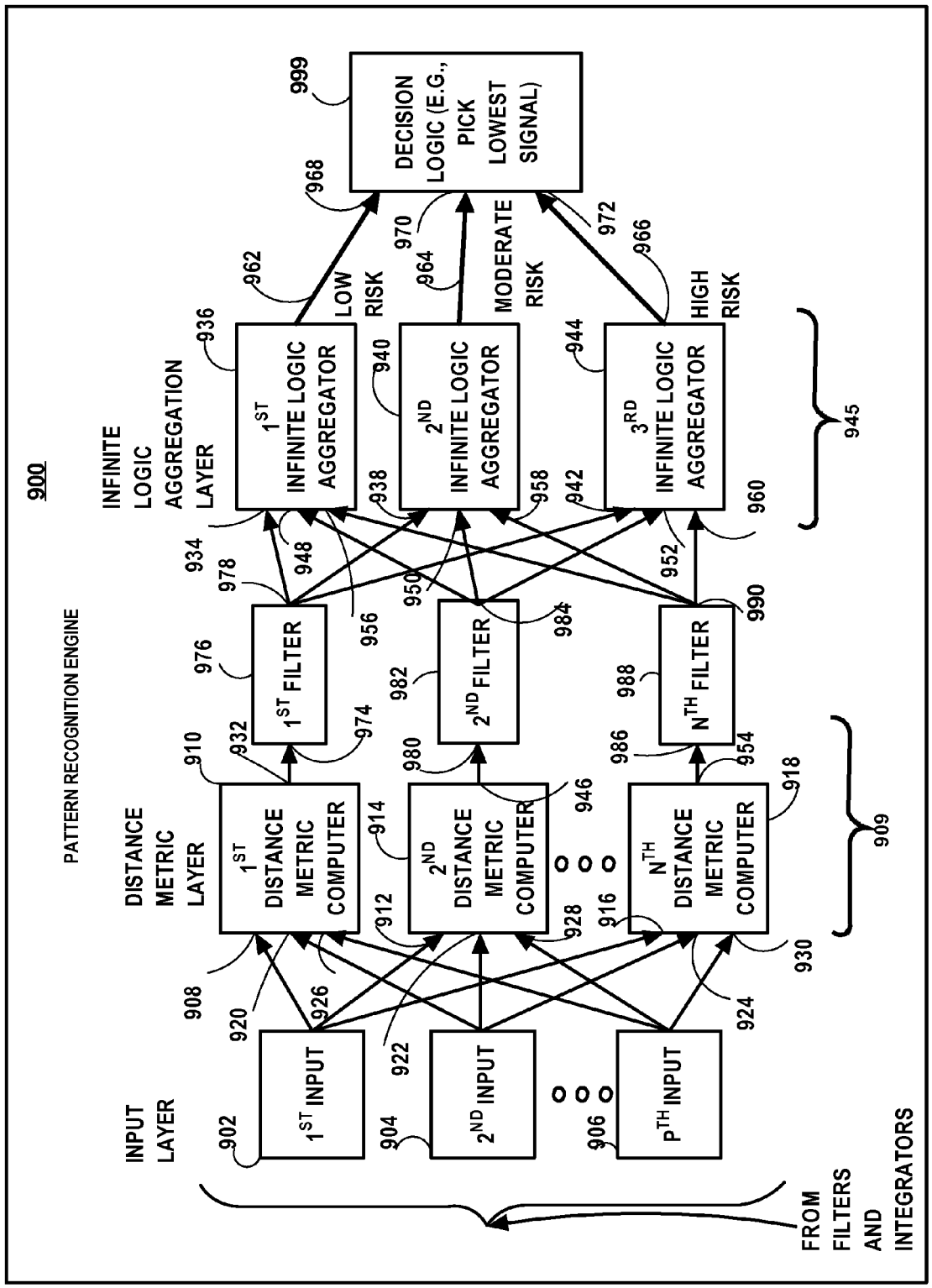
FIG. 9 is a pattern recognition engine that is used in the risk management signal processor shown in FIG. 7 according to an embodiment of the invention.

FIG. 9 is a pattern recognition engine 900 that is used in the risk management signal processor shown in FIG. 7 according to an embodiment of the invention. As shown in FIG. 9 the pattern recognition engine 900 comprises a first pattern recognition engine input 902, a second pattern recognition engine input 904 up to a $P^{TH}$ pattern recognition engine input 906. Component of the feature vector including signals output by the derivative filters 704, full call duration integrators 708, short time interval noise removal filters 710 and the sensors at the scene of the incident 212; and the stored data on the first responder 602 are coupled to the pattern recognition engine inputs 902, 904 906. Although only three pattern recognition engine inputs 902, 904, 906 are shown for purposes of illustration, it should be understood that in fact there is a separate input for each feature vector component (signal or data item). Generally, the number of pattern recognition engine inputs is equal to the dimensionality of the feature vectors.

The first pattern recognition engine input 902 is connected to a first input 908 of a first distance metric computer 910, a first input 912 of a second distance metric computer 914 and a first input 916 of an $N^{TH}$ distance metric computer 918. Similarly, the second pattern recognition engine input 904 is connected to a second input 920 of the first distance metric computer 910, a second input 922 of the second distance metric computer 914 and a second input 924 of the $N^{TH}$ distance metric computer 918; and the $P^{TH}$ pattern recognition engine input 906 is connected to a $P^{TH}$ input 926 of the first distance metric computer 910, a $P^{TH}$ input 928 of the second distance metric computer 914 and a $P^{TH}$ input 930 of the $N^{TH}$ distance metric computer 918. The distance metric computers 910, 914, 918 form a hidden layer 909 of the pattern recognition engine 900. Each distance metric computer 910, 914, 918 computes a distance of an input feature vector from a point (center) in the feature vector space (e.g., a cluster center). The centers in the feature vector space can, for example, typify high risk, or medium risk combinations of sensor readings. The distance function to be used may be Euclidean, weighted Euclidean, P-metric, Mahalanobis distance, or a distance computed by another distance metric. One metric that may be used is taught in co-pending patent application Ser. No. 11/554,643 entitled "System for Pattern Recognition with Q-metrics", filed Oct. 30, 2006 and is given by the following equation:

$$d_{\lambda_D}(x, y) = \frac{\prod_{i=1}^{P} (1 + \lambda_D w_i |x_i - y_i|) - 1}{P\lambda_D} \quad \text{EQU. 7}$$

where, $\lambda_D \in [-1,0)$ is a metric control parameter;

$x_i \in [0,1]$ is an $i^{th}$ component of an input feature vector denoted x $y_i \in [0,1]$ is an $i^{th}$ component of a feature vector reference point (e.g., cluster center) denoted y;

P is the dimensionality of feature vector space;

$w_i \in [0,1]$ is an $i^{th}$ dimension weight; and $d_{\lambda_D}(x,y) \in [0,1]$ is a per-unit distance between the input feature vector and the feature vector center.

Using a weighted distance metric allows input signals to be selectively emphasized or de-emphasized. An output 932 of the first distance metric computer 910 (at which a computed distance is output) is coupled to an input 974 of a first filter 976. An output 978 of the first filter 976 is coupled to a first input 934 of a first infinite logic aggregator 936, a first input 938 of a second infinite logic aggregator 940, and a first input 942 of a third infinite logic aggregator 944. Similarly an output 946 of the second distance metric computer 914 is coupled to an input 980 of a second filter 982 and an output 984 of the second filter 982 is coupled to a second input 948 of the first infinite logic aggregator 936, a second input 950 of the second infinite logic aggregator 940 and a second input 952 of the third infinite logic aggregator 944; and an output 954 of the $N^{TH}$ distance metric computer 918 is coupled to an input 986 of an $N^{TH}$ filter 988 and an output 990 of the $N^{TH}$ filter 988 is coupled to an $N^{TH}$ input 956 of the first infinite logic aggregator 936, a $N^{TH}$ input 958 of the second infinite logic aggregator 940 and a $N^{TH}$ input 960 of the third infinite logic aggregator 944. The filters 976, 982, 988 can comprise Q-filters, fast Q-filters or other filters such as FIR, IIR, for example. In any case the filters 976, 982, 988 provide additional noise reduction and may also effectively alter the real-time processing decision boundaries established by the pattern recognition engine 900. Alternatively, the filters 976, 982, 988 are not used. The infinite logic aggregators 936, 940, 944 form an output layer 945 of the pattern recognition engine 900. The first, second and third infinite logic aggregators 936, 940, 944 have a first output 962, a second output 964 and a third output 966 respectively and these outputs 962, 964, 966 are coupled to a first input 968 a second input 970 and a third input 972, respectively of a decision logic block 999. Each of the aggregators 936, 940, 944 is associated with a particular state (e.g., low risk, medium risk, high risk) that the pattern recognition engine 900 is capable of recognizing. The decision logic 999 suitably outputs as a recognized state the state associated with the aggregator that produced the lowest output. (If the distance metric computers 910, 914, 918 were replaced by Gaussians functions or other monotonic decreasing functions of feature vector space distance (e.g., similarity functions), it would be appropriate to have the decision logic output the state associated with the aggregator that produced the highest output.)

The infinite logic aggregators 936, 940 944 can implement a variety of infinite logic rules for combining the distances computed by the distance metric computers 910, 914, 918 in order to judge whether a measured subject belongs to a classification. Expressed in words, such rules include, for example: "close to at least one of a select group of cluster centers", "close to all of a select group of cluster centers", "close to one cluster center but far from another cluster center" or "far from all cluster centers".

According to one embodiment the infinite logic aggregators use a composition of the aggregation function given by equation 6 on a veracity function that is a weighted sum of the identity function and an infinite logic inverter function. The veracity function allows a positive, negative, or no inference to be made based on the distance of an input feature vector from a particular feature vector center used by one of the distance metric nodes 910, 914, 918. The aggregation function given by equation 6 allows the output of the veracity function for multiple distance metric nodes 910, 914, 918 to be combined with an infinite logic function ranging from disjunctive (fuzzy union connective) to conjunctive (fuzzy intersection connective).

One suitable form of infinite logic inverter is given by:

$$Inv_\beta(d) = \begin{cases} \frac{1-d}{1+\beta d} & d \neq 1 \\ 0 & d = 1 \end{cases} \quad \text{EQU. 8}$$

where, $d \in [0,1]$, is a feature vector space distance value;
$\beta \in [-1,+\infty)$, is a nonlinearity control parameter; and
$Inv_\beta(d) \in [0,1]$ is the output of the infinite logic inverter.
One suitable form of veracity function is given by:

$$Ver(\alpha,\beta,d) = \alpha d + (1-\alpha)Inv_\beta(d) \quad \text{EQU. 9}$$

where, $d \in [0,1]$, is a feature vector space distance value;
$\alpha \in [0,1]$ is a veracity control parameter;
$Ver(\alpha,\beta,d) \in [0,1]$ is the output of the veracity function.
Composing the aggregation function given by equation six on the veracity function yields:

$$A_{\lambda_A}(d_1, \ldots, d_n) = \quad \text{EQU. 10}$$

$$\begin{cases} \dfrac{\prod_{i=1}^{n}(1+\lambda_A \cdot Ver(\alpha_i, \beta_i, d_i)) - 1}{\prod_{i=1}^{n}(1+\lambda_A) - 1} & \lambda_A \geq -1, \lambda_A \neq 0 \\ \dfrac{1}{n}\sum_{i=1}^{n} Ver(\alpha_i, \beta_i, d_i) & \lambda_A = 0 \end{cases}$$

where, $d_i$ is the $i^{th}$ per-unit distance values (e.g., produced by one of the distance metric computers 910, 914, 918);
$\alpha_i \in [0,1]$ is the veracity control parameter for the $i^{th}$ distance;
$\beta_i \in [-1,+\infty)$, is the nonlinearity control parameter for the $i^{th}$ distance, and $Ver(\alpha_i,\beta_i,d_i) \in [0,1]$ is the value of the veracity function for the $i^{th}$ distance;
$\lambda_A \geq -1$ is the connective control parameter; and
$A_{\lambda_A}(d_1, \ldots, d_n)$ is the output of one of the infinite logic aggregator 936, 940, 944.

As shown in FIG. 9 each pattern recognition input 902, 904, 906 is connected to all of the distance metric computers 910, 914, 918 and each distance metric computer 910, 914, 918 is connected to all of the infinite logic aggregators 936, 940, 944. This is termed fully connected. Alternatively, the pattern recognition engine 900 is not fully connected.

Co-pending patent application Ser. No. 11/554,734 entitled "Configurable Infinite Logic Signal Processing Network and Genetic Computing Method of Designing the Same" to Magdi Mohamed et al discloses networks that include one or more adaptable infinite logic connective signal processors in combination with one or more infinite logic inverters forming an infinite logic network. As disclosed in that application the topology of the network can be determined by a Gene Expression Programming (GEP) algorithm that uses a hybrid Genetic Algorithm (GA)/Differential Evolution (DE) subprogram to learn control parameter values. According to an alternative embodiment of the invention such infinite logic networks are used in the pattern recognition engine 900 in place of the infinite logic aggregators 936, 940, 944.

Although, parameters of pattern recognition engines are typically determined by numerical optimization in the course of training with labeled feature vectors, the pattern recognition engine 900 works in an intuitively understandable manner, so that plausible values of at least some of the parameters, i.e., feature vectors space centers y, parameters $\alpha_i$, $\lambda_A$ and some of the $\beta_i$ values can be deduced. The values that are deduced can be used as initial values that are further refined by optimization in the course of training. For example, one can select several feature vector space centers y that characterize combinations of signal levels (e.g., high body temperature, in combination with high heart rate, low blood oxygen, etc) which represent "high risk" conditions, and several that represent "medium risk" conditions. For the third infinite logic aggregator 944 that identifies the "high risk" state, the parameters $\alpha_i$ for distances to vector space centers that characterize "high risk" can be set/initialized to zero and $\lambda_A$ set/initialized to a high value (e.g., 100) so that if an input feature vector is close to any of the feature vector space centers y associated with high risk the output of the third infinite logic aggregator 944 will be low. Furthermore, for the third infinite logic aggregator 944 that identifies the "high risk state" the $\alpha_i$ and $\beta_i$ for distances to vector space centers that characterize "medium risk" can be set/initialized to ½ so that the output of the third infinite logic aggregator is neutral with respect to distances to the "medium risk" feature vector space centers. Analogous settings/initializations can be used for the second infinite logic aggregator 940 that identifies "medium risk" conditions. For the first infinite logic aggregator 936 that identifies the "low risk" condition, the parameters $\alpha_i$ corresponding to all distance to the "high risk" feature vector space centers y, and the "medium risk" feature vector space centers can be set to 0 and $\lambda_A$ set/initialize to −1. With such settings, the output of the first infinite logic aggregator will only be low (strongly TRUE) if the input feature vector is far from feature vector centers y associated with "medium risk" and "high risk". With these settings the "low risk" condition is regarded as a kind of default if the combination of conditions represented in the input feature vector is not "medium risk" or "high risk". Optimization can then be applied to refine the initial settings of these parameters using training data.

Other parameters such as the remaining $\beta_i$ parameters of the aggregators 936, 940, 944, the $\lambda_D$ parameters for the distance metric computers 910, 914, 918, and the parameters $\{\lambda_{fi}, f_i\}$ of the filters 976, 982, 988 can be determined by optimization in training as well.

The above description of the pattern recognition engine 900 in considerable detail should not be construed as implying that this particular pattern recognition engine is indispensable for the system 100. Persons having ordinary skill in the art of pattern recognition will recognize that any number of known pattern recognition engines, including but not limited to: Linear Discriminants, Quadratic Discriminants, Gaussian Mixtures, Hidden Markov Models, K-Nearest Neighbor, Support Vector Machines, Artificial Neural Networks, Tree Based Classifiers, Expert Systems, or Fuzzy Logic methods, can be used, with some level of success, in the intelligent risk assess system for first responders 100 in lieu of the pattern recognition engine 900.

Figure 10:
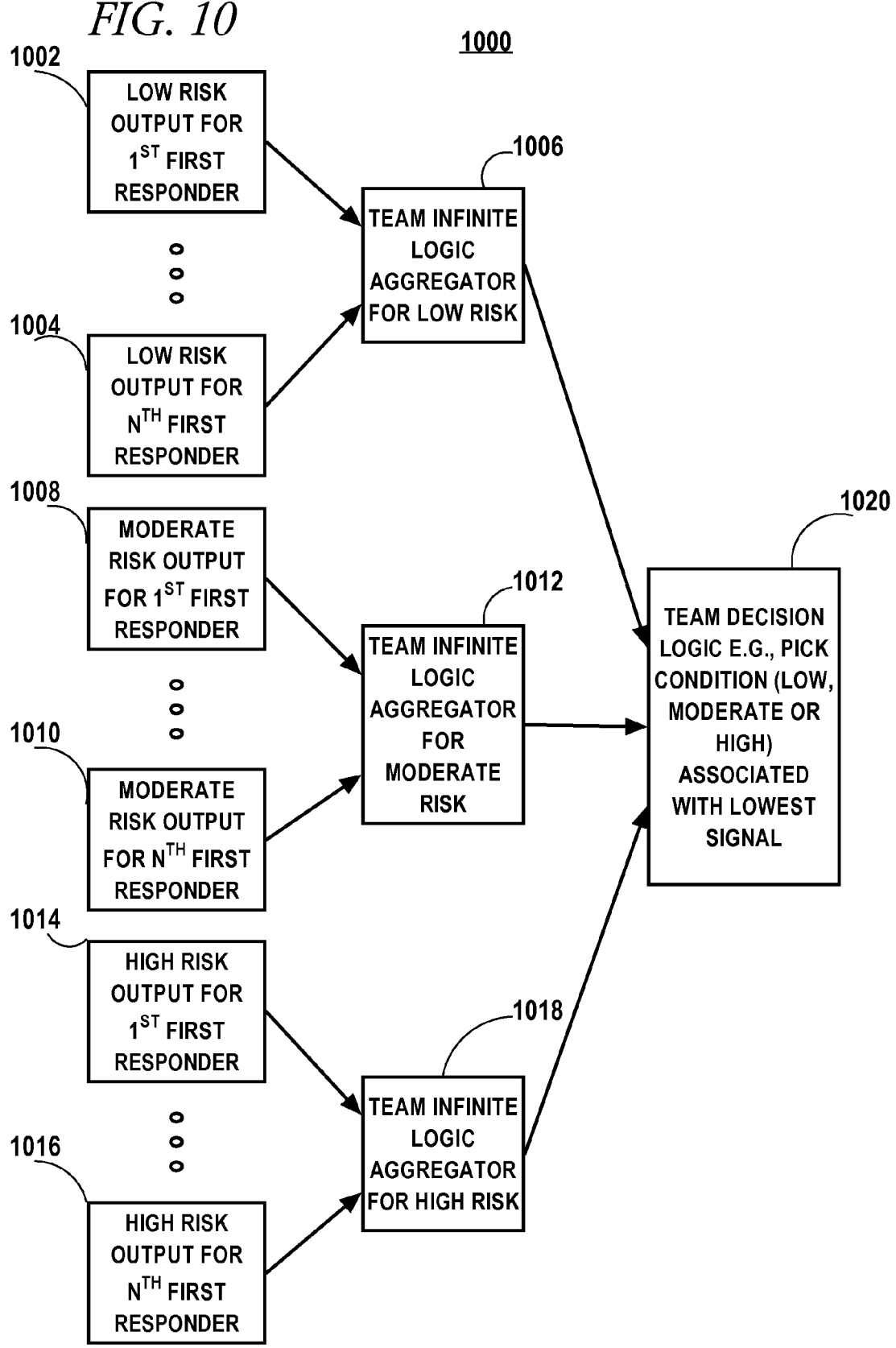
FIG. 10 is a network of team aggregators that is used to aggregate risk assessments for individual first responders into a team risk assessment.

FIG. 10 is a network of team aggregators 1000 that is used to aggregate risk assessments for individual first responders into a team risk assessment. If the team risk assessment indicates high risk to a team of first responders, the commander may decide to withdraw the team or send in additional first responders to help out. The network of team aggregators 1000 receive inputs from multiple pattern recognition engines, each of which processes data for a single first responder. In the case of the pattern recognition engine 900 shown in FIG. 9 the signals for the network of team aggregators 1000 are taken from the infinite logic aggregators 936, 940, 944 i.e., before the decision logic 999 reduces continuous output of the infinite logic aggregators 936, 940, 944 to a hard risk state. In particular, a low risk output 1002 (e.g., the output 962 of the first infinite logic aggregator 936) for a first responder through a low risk output 1004 of an $N^{TH}$ first responder on the team of first responders are coupled to a team infinite logic aggregator for low risk 1006. Similarly a moderate risk output 1008 (e.g., the output 964 of the second infinite logic aggregator 940) for a first first responder through a moderate risk output 1010 for the $N^{TH}$ first responder are coupled to a team infinite logic aggregator for moderate risk 1012; and a high risk output 1014 (e.g., the output 966 of the third infinite logic aggregator 944) for a first responder through a high risk output 1016 for the $N^{TH}$ first responder are coupled to a team infinite logic aggregator for high risk 1018. The team infinite logic aggregators 1006, 1012, 1018 can implement (e.g., by programmed processor, or specialized circuits) equation six. In using equation six, if zero rather than one is taken to represent the strongest "TRUE" value, then conjunctive operations become disjunctive and vice versa. Thus, the team infinite logic aggregators 1006, 1012, 1018 can combine the signals from the individual team member's pattern recognition engines using disjunctive infinite logic (similar to the MAX function), conjunctive infinite logic (similar to the MIN function) or a function between these, e.g., signal averaging (or another compensative operation). To err on the side of caution, i.e., to bias the team risk state assessments to higher levels of risk, the team infinite logic aggregator for high risk 1018 can be configured to approximate the MIN function and the team infinite logic aggregator for low risk 1006 can be configured to approximate the MAX function. These choices assume that the individual pattern recognition engines 900 identify the prevailing risk condition based on the infinite logic aggregator 936, 940, 944 that produced the lowest output. The settings of the team infinite logic aggregators 1006, 1012, 1018 can also be learned using feature vector data for an entire team that is labeled based on positive, negative, and very negative outcomes of first responder calls. Outputs of the team infinite logic aggregators 1006, 1012, 1018 are coupled to a team decision logic 1020. The team decision logic outputs a team risk state assessment (e.g., "low risk", "moderate risk" or "high risk"). Assuming that the decision logic 999 for the pattern recognition engines 900 for the individual first responders select the risk state assessment based on the lowest input signal, the team decision logic can select the team risk state assessment based on the team infinite logic aggregator 1006, 1012, 1018 that produced the lowest signal as well.

Figure 11:
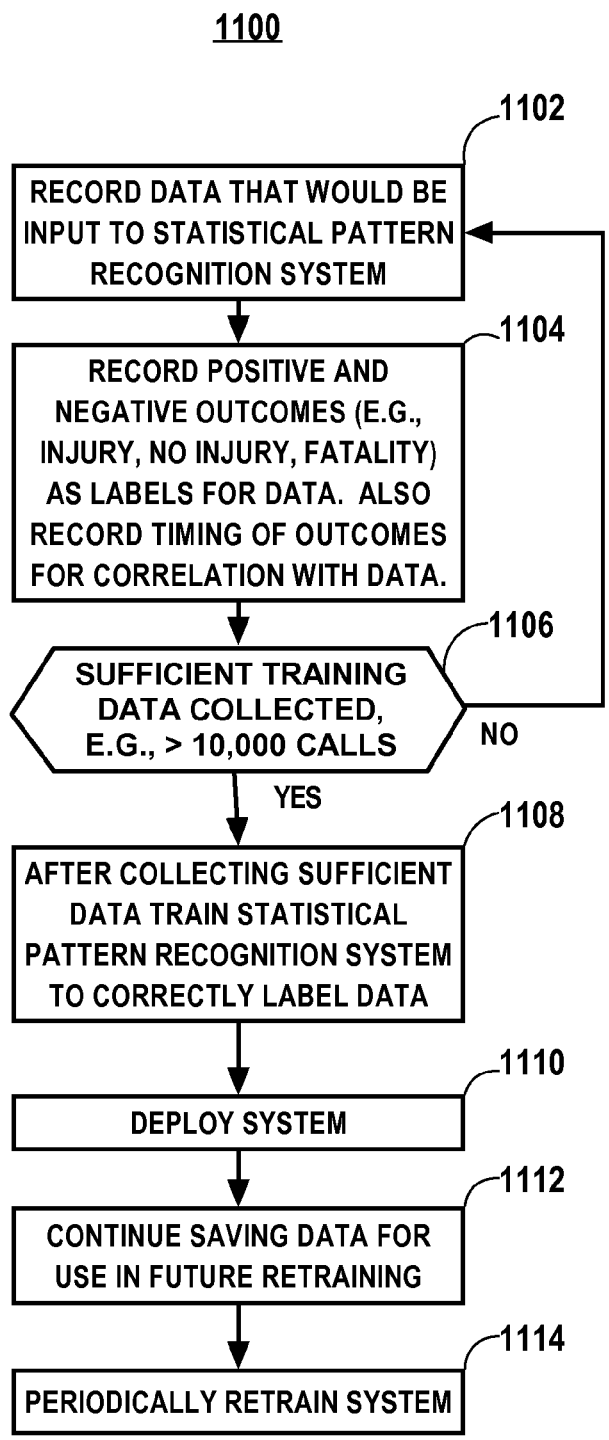
FIG. 11 is a flowchart of a training regimen for a pattern recognition engine used in the risk management signal processor, and optionally for other configurable (trainable) parts of the intelligent risk management system for first responders.

FIG. 11 is a flowchart 1100 of a training regimen for the pattern recognition engine 900, 402 used in the risk management signal processor 206 and optionally for other configurable (trainable) parts of the intelligent risk management system 100 for first responders. Other configurable parts of the intelligent risk management system that may be trained include the filters 318 and signal aggregators 320 in the first responder's portable data pre-processors 202 and parts of the feature vector extraction system 704. In block 1102 data that would be input into the pattern recognition engine 402, 900 is recorded for use in training. Training data from the sensors on the first responder 104 the sensors at the scene of the incident 212 are recording during emergency response activities. In block 1104 positive outcomes (e.g., no injuries incurred) and negative outcomes, (e.g., injuries or fatalities incurred) of emergency response activities are recorded as labels for the data collected in block 1104. Timing information for injuries and fatalities is also recorded so that the labels can be correlated with the data from the sensors 104, 212 which is times series type data. Injuries and fatalities may sometimes occur or be discovered sometime after exposure hazardous conditions and stresses. Therefore, in some cases it may be necessary to record an earlier time for negative outcomes. The exact earlier time that is associated with a negative outcome label may be somewhat subjective, but the choice of the earlier time can be informed by reviewing the time series data from the sensors and interviewing first responder witnesses. The negative outcomes may be divided into two categories one associated with mild injuries (e.g., those only requiring treatment at scene of incident) can be labeled "moderate risk" and another associated with more acute injuries (e.g., requiring hospitalization) or fatalities can be labeled "high risk". If no negative outcomes occur during a first responder call, then feature vectors collected at regular intervals during the call (e.g., every 15 seconds) are labeled "low risk".

Decision block 1106 tests if sufficient training data has been collected. Typically more training data feature vectors are required for higher dimensionality feature vector spaces. If the outcome of block 1106 is negative then the flowchart 1100 loops back to block 1102 and continues collecting training data as previously described. If, on the other hand, sufficient training data has been collected, then in block 1108 the pattern recognition engine 900, 402 is trained to correctly label the feature vectors in the feature vector space. Then, after training, in block 1110 the system is fully deployed, with the pattern recognition engine 900, 402 actively assessing the risk state of first responders responding to emergency calls. In block 1112 the system continues saving data for use in future retraining which is performed periodically as indicated in block 1114.

The pattern recognition engine 900 can, for example, be trained using differential evolution with an objective function that depends on a number of incorrect classifications and correct classifications (e.g., the ratio of the two). A higher weight may be given to incorrect classifications of feature vectors labeled "high risk" because of the criticality of avoiding misclassification of such conditions and because the relative infrequency of such "high risk" labeled data.

Figure 12:
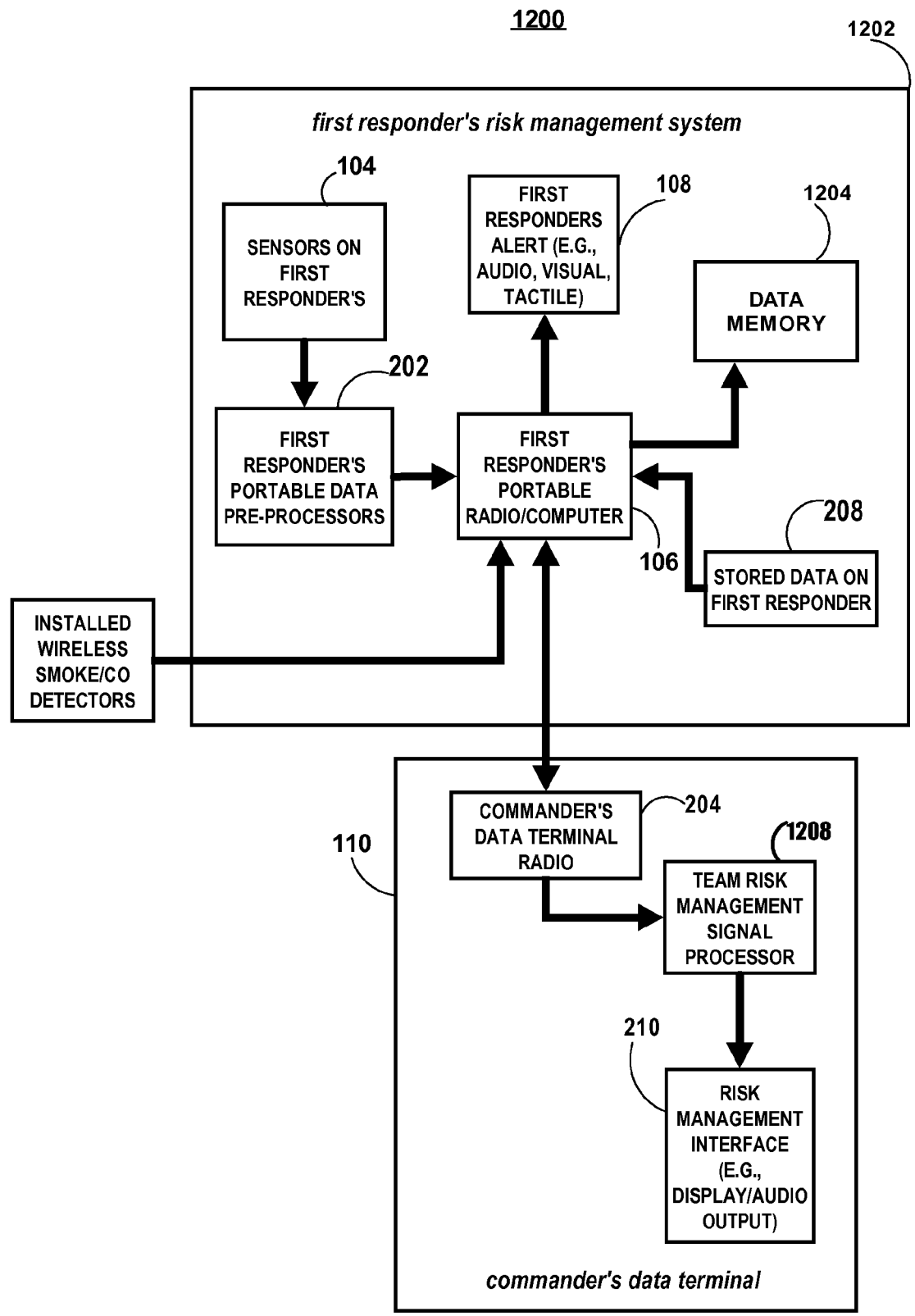
FIG. 12 is a block diagram of an intelligent risk management system for first responders according to an alternative embodiment of the invention.

FIG. 12 is a block diagram of the intelligent risk management system for first responders 1200 according to an alternative embodiment of the invention. The system 1200 includes a first responder's risk managements system 1202 that is largely autonomous. The risk management signal processor 206 is implemented in software and/or hardware in the first responder's portable radio computer 106, which can be a device such as the HDT600 handheld data terminal. The first responder's portable radio/computer 106 is coupled to a data memory 1204 that is used to log sensor data. Storing sensor data allows for later review and use of the data in future training of the pattern recognition engine 900, 402. The first responder's portable radio/computer 106 can also be wirelessly connected to installed wireless smoke and/or carbon monoxide sensors 1206. According to this embodiment, even if the first responder's portable radio/computer 106 cannot establish a communication channel with the commander's data terminal 110 the first responder 102 will still have access to information from the risk management signal processor 206 because it is carried with the first responder 102. In addition to implementing the risk management signal processor 206 locally, the first responder's portable radio/computer 106 can also transmit pre-processed sensor data and information relative to the first responder's risk state (e.g., the output of the infinite logic aggregators 936, 940, 944 and the decision logic 999) to the commander's data terminal 110. The commander's data terminal 110 includes a team risk management signal processor 1208, which can be used to implement the network of team aggregators 1000 in software and/or hardware. If the commander's data terminal 110 has radio connections with a sufficient (pre-programmed) fraction of the first responders, the supervisory risk management signal processor can run the network of team aggregators 1000 to obtain the team risk assessment.

Figure 13:
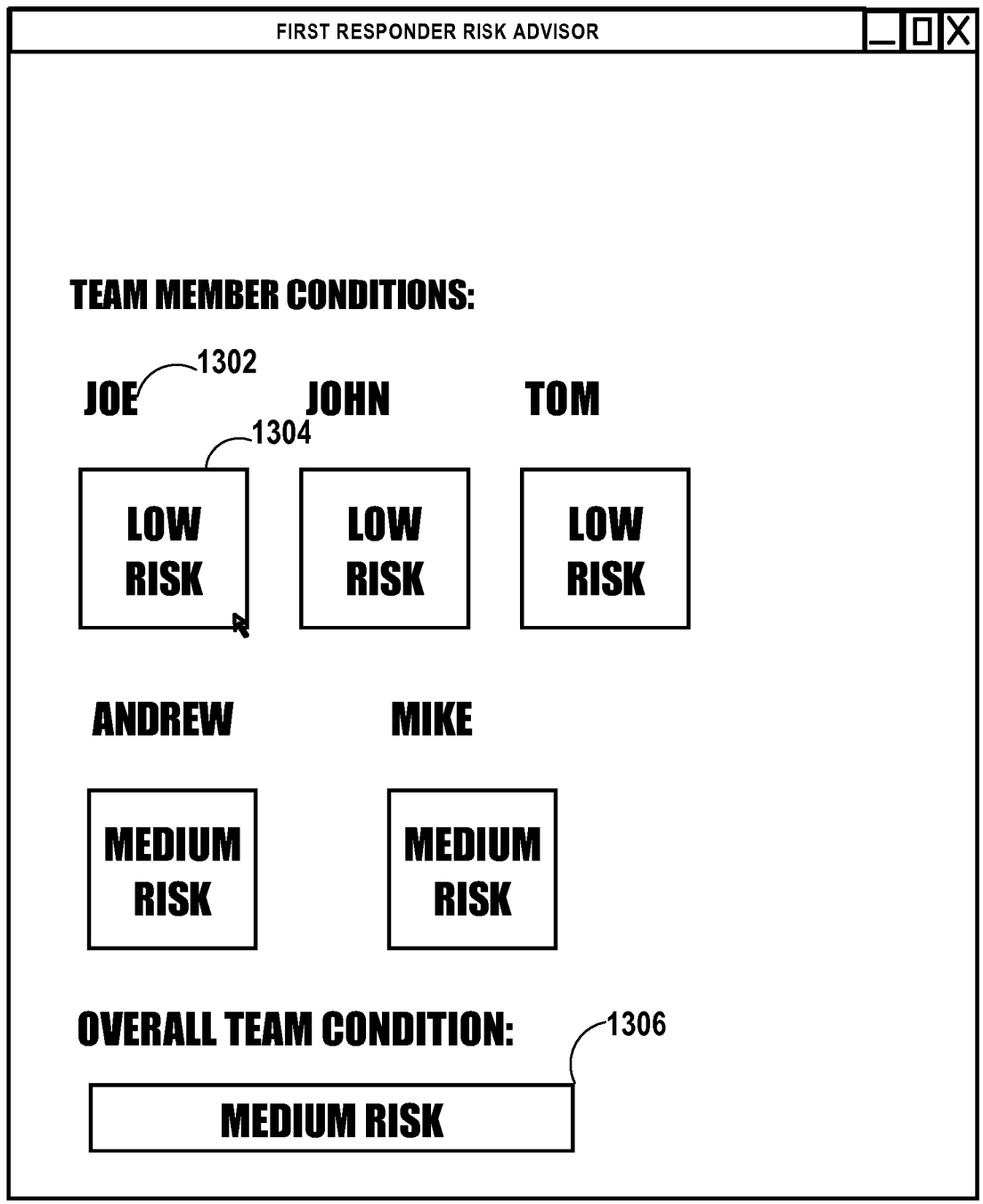
FIGS. 13-15 depict three windows of a Graphical User Interface (GUI) of the intelligent risk management system for first responders shown in FIGS. 1, 12 according to an embodiment of the invention.
Figure 14:
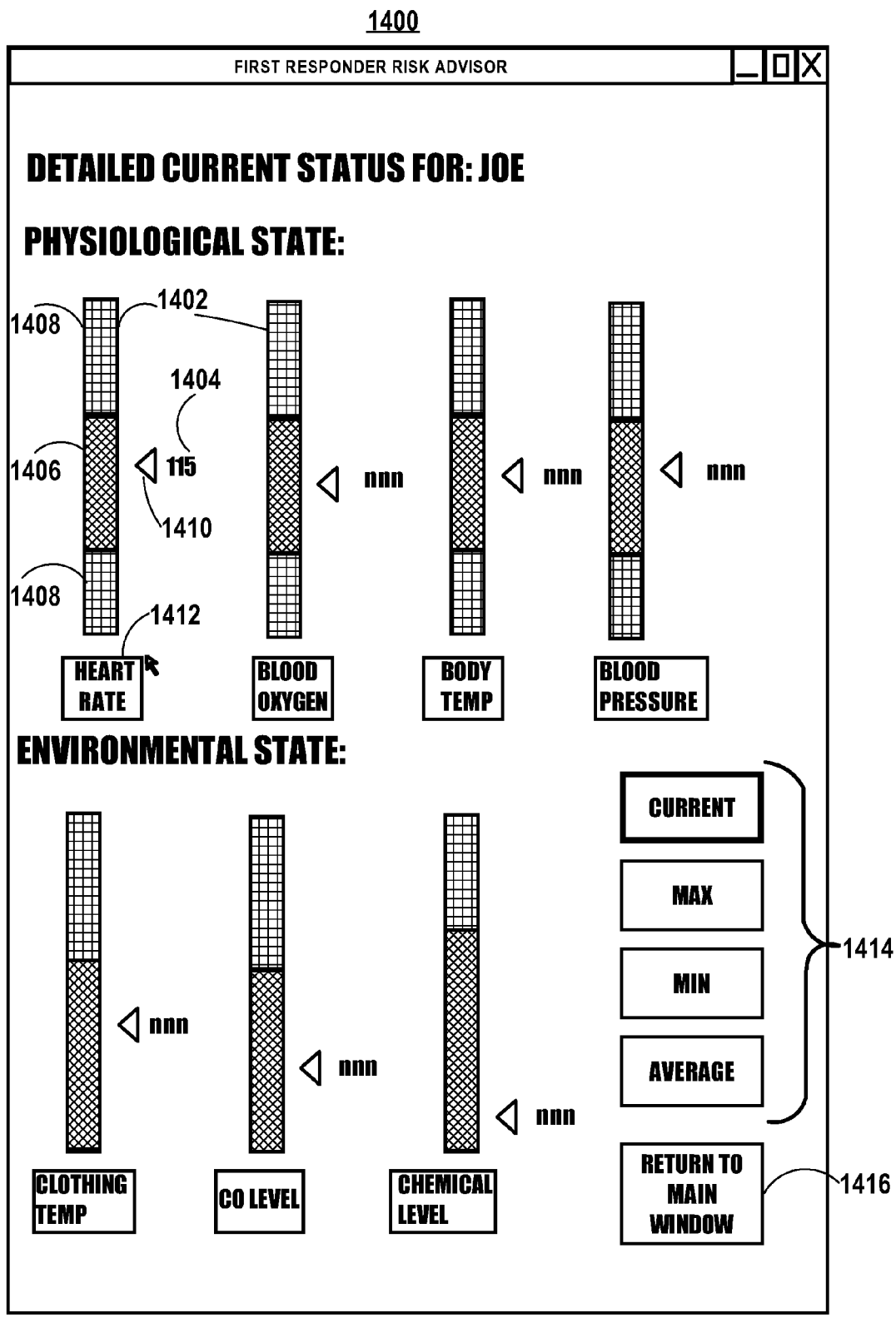
Figure 15:
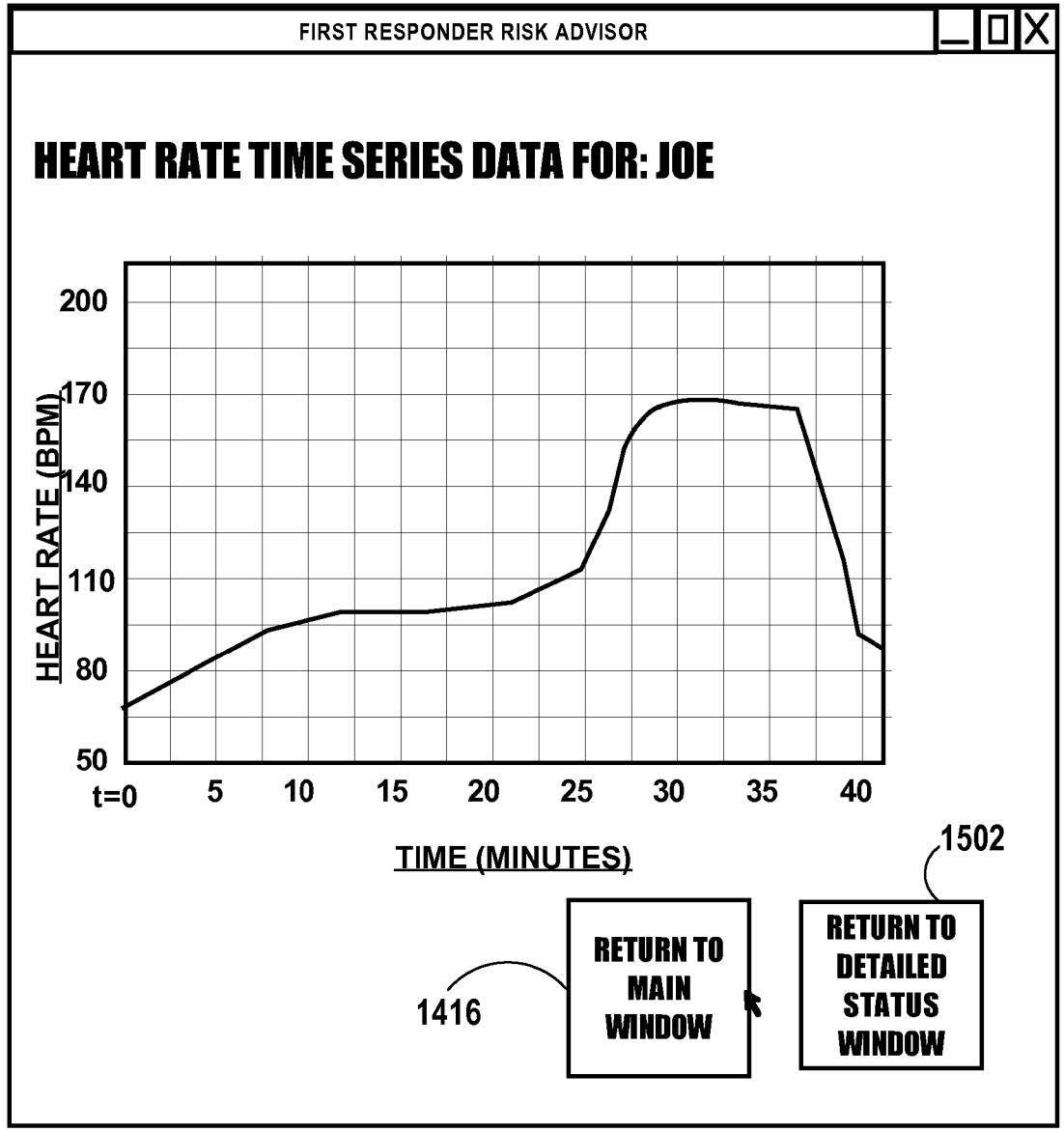

FIGS. 13-15 depict three windows of a Graphical User Interface (GUI) of the intelligent risk management systems for first responders 100, 1200 shown in FIGS. 1, 12 according to an embodiment of the invention. The GUI is part of the risk management interface 210 of the commander's data terminal 110. A first window 1300 summarizes the status of a team of first responders under the commander's command. The name of each first responder 1302 is listed above a clickable button 1304 that indicates the current risk assessment (e.g., "low risk", "high risk", "medium risk") for the named first responder. The current risk assessment is based on the output of the decision logic 999 or the output of alternative pattern recognition engines. The overall team risk assessment is given in a separate box 1306. The overall team risk assessment is based on the output of the team decision logic 1020. Clicking one of the clickable buttons 1304 for the individual first responders will bring up a second window 1400 shown in FIG. 14 which gives sensor readouts for the selected first responder in bar graph form 1402 along with numerical readouts 1404. Safe ranges 1406 and unsafe ranges 1408 are shown in different colors. A pointer 1410 indicates a level of each sensor read-out on the bar graph 1402. The type of reading given by each sensor read-out is listed in a clickable box 1412. Clicking one of the clickable boxes 1412 brings up a third window 1500 that shows times series data for the sensor identified by the clicked clickable box 1412. The second window also includes a set of buttons 1414 for selecting a current reading, maximum reading (over the entire first responder call), a minimum reading or an average reading. The first window 1300 presents essential information in concise form for use by the commander during a first responder call. The third window 1500 includes information for review and analysis after the first responder call is over. Both the second window 1400 and the third window 1500 include a button 1416 for returning to the first window 1300. The third window also includes a button 1502 for returning to the second window 1400.

Figure 16:
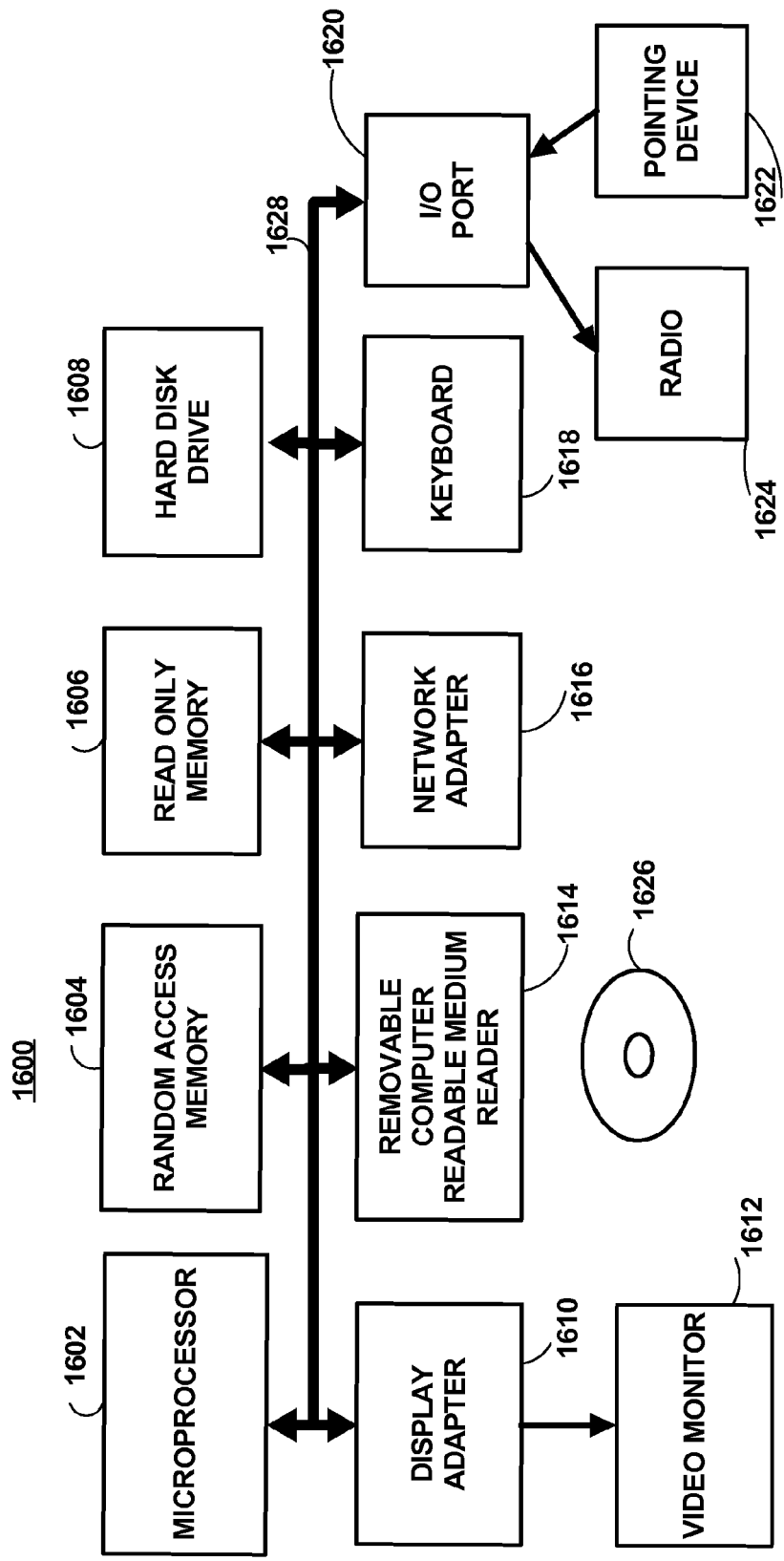
FIG. 16 is a block diagram of a computer used in the intelligent risk management system for first responders shown in FIG. 1 according to an embodiment of the invention.
Figure 17:
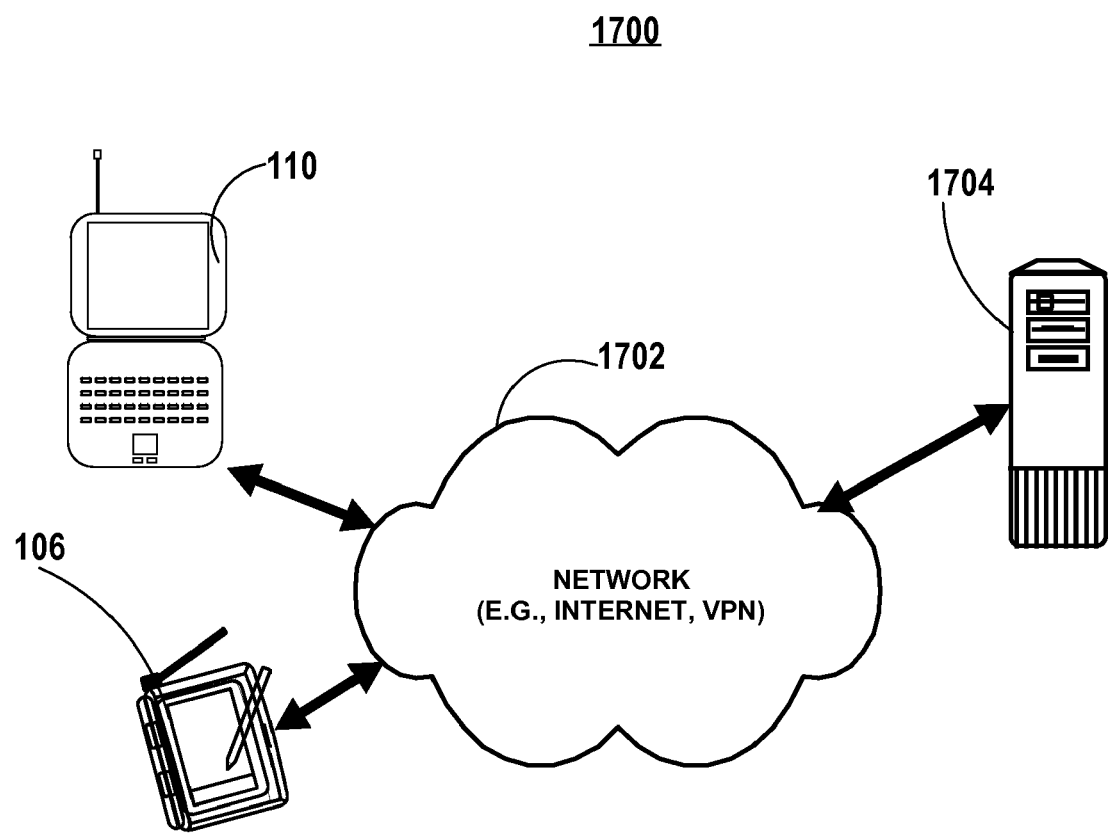
FIG. 17 shows a network distributed architecture used by the intelligent risk management system for first responders shown in FIG. 1 according to an embodiment of the invention

FIG. 16 is a block diagram of a computer 1600 (e.g., 106, 110) used in the intelligent risk management system for first responders shown in FIG. 1 according to an embodiment of the invention. The computer 1600 comprises a microprocessor 1602, Random Access Memory (RAM) 1604, Read Only Memory (ROM) 1606, hard disk drive 1608, display adapter 1610, e.g., a video card, a removable computer readable medium reader 1614, a network adaptor 1616, a keyboard 1618, and an I/O port 1620 communicatively coupled through a digital signal bus 1628. A display monitor 1612 is electrically coupled to the display adapter 1610 for receiving a video signal. A pointing device 1622, e.g., a touchpad, is coupled to the I/O port 1620 for receiving signals generated by user operation of the pointing device 1622. A radio 1624 is also coupled to the I/O port 1620. The network adapter 1616 can be used, to communicatively couple the computer 1600 to a remote server (1704, FIG. 17). The computer readable medium reader 1614 preferably comprises a Compact Disk (CD) drive. A computer readable medium 1626 that includes software embodying the programs described above is provided. The software included on the computer readable medium 1626 is loaded through the removable computer readable medium reader 1614 in order to configure the computer 1600 to carry out programs of the current invention that are described above with reference to the FIGs. The computer 1600 may for example comprise a laptop computer or handheld size data terminal. Computer readable media used to store software embodying the programs described above can take on various forms including, but not limited to, magnetic media, optical media, and semiconductor memory FIG. 17 shows a network distributed architecture 1700 used by the intelligent risk management system for first responders 100 according to an embodiment of the invention. As shown in FIG. 17, the commander's data terminal 110 and/or the first responder's portable radio/computer 106 are coupled by a network 1702 (e.g., the Internet, or a Virtual Private Network (VPN)) to a server 1704. Feature vector data and optionally labels assigned by local first responder departments are transmitted via the network 1702 to the server 1704. The server is used to perform training of the pattern recognition engine 402, 900 and optionally other parts of the system 100, as per block 1108 of FIG. 11. Configuration parameters for the pattern recognition engine 402, 900 and optionally other parts of the system 100 are from time to time transmitted back to the commander's data terminal 110 and/or the first responder's portable radio/computer 106 and used to configure the system 100. Operation of the server 1704 may for example be run by a state or federal government bureau, government contractor or other commercial entity that offers services directly to first responder departments. The network distributed architecture allows for efficient collection of large amounts of training data which benefits training of the system 100. Moreover, different first responder departments will benefit if the risk management system for first responders is trained based on the experiences of many different first responder departments.

Figure 18:
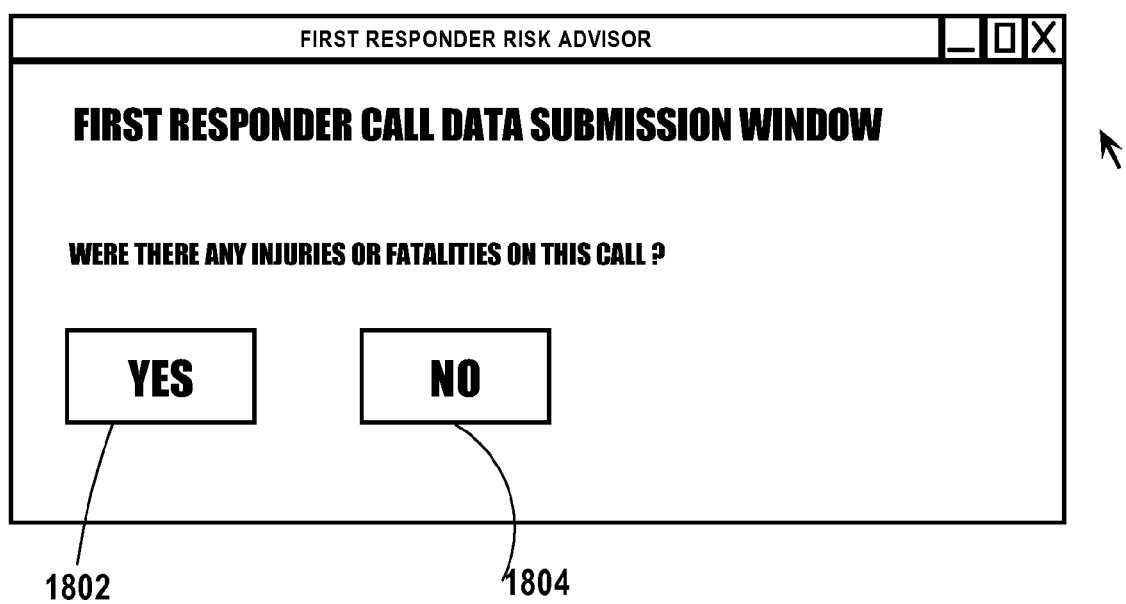
FIGS. 18-19 depict two additional GUI windows of the intelligent risk management system for first responders shown in FIGS. 1, 12 according to an embodiment of the invention.
Figure 19:
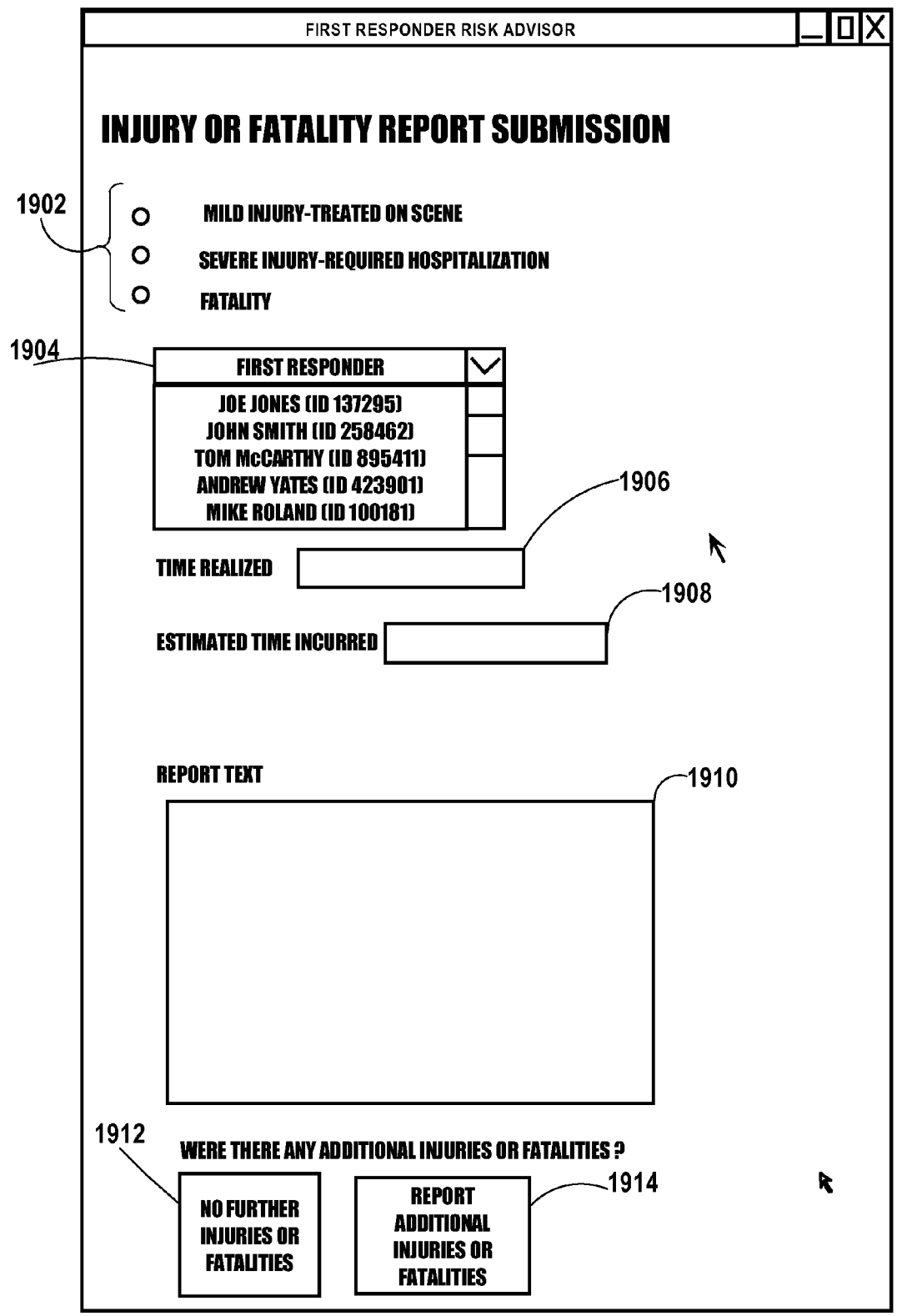

FIGS. 18-19 show a fourth GUI window 1800 and a fifth GUI window 1900 that are used to submit labeled feature vectors to the server 1704. The fourth and fifth windows 1800, 1900 can be used by the commander after a first responder call has been concluded. The fourth window 1800 presents a question as to whether any injuries or fatalities occurred during the call along with a clickable "YES" button 1802 and a clickable "NO" button 1804. If the "NO" button 1804 is clicked, then all of the feature vectors collected from all the first responders during the call will be labeled (or assumed to be) "low risk" and sent through the network 1702 (e.g., using the network adapter 1616) to the server 1704. If the "YES" button 1802 is clicked, then an instance of the fifth window 1900 will be opened. The fifth window 1900 is used to collect information on the injury or fatality that occurred. A set of radio buttons 1902 allows the commander to indicate a mild injury-treated on the scene, a severe injury-requiring hospitalization, or a fatality. According to one design a mild injury invokes "medium risk" feature vector labels and a severe injury or fatality invokes "high risk" feature vector labels. A pull down menu 1904 is used to select a name (and/or ID) of a first responder that suffered the injury or loss of life. A first text box 1906 is used to enter a time that the injury or fatality was reported and a second text box 1908 is used to enter an estimated time that the injury or fatality occurred. The time from the second box 1908 can be used to identify feature vectors that should be labeled as "medium risk" or "high risk", as the case may be. For example, feature vector data within a predetermined interval preceding the time reported in the second box 1908 can be automatically labeled "medium risk" or "high risk" depending on the selected radio button 1902. After the data is submitted a qualified person, e.g., a doctor, may review feature vector data preceding the time entered in box 1906 or 1908 and label such data as "medium risk" or "high risk" at his or her discretion. A third text box 1910 provides space for a written report to be submitted. Such a written description may be useful deciding whether feature vector data should be relabeled and can also be used for other reporting purposes. Below the third text box 1910 a first clickable button 1912 is used to indicate that there are no further injuries or fatalities to report, and a second clickable button 1914 is used to indicate that there are additional injuries or fatalities to report. Clicking the second button 1914 results in another instance of the fourth window 1900 being opened so that information on further injuries or fatalities can be collected. Clicking the first button 1912 causes labeled feature vectors collected from all the first responders during the call being to be submitted through the network 1702 (e.g., using the network adapter 1616) to the server 1704. It is not necessary to transmit the names of the first responders to the server 1704, therefore there need not be any concern that use of the systems 100, 1200 encroach on medical privacy.

The systems 100, 1200 can also be used to safeguard other personnel involved in high physical stress occupations, including for example, mine workers, military personnel undergoing intensive training and underwater workers. For use in underwater environments, acoustic modems can be used in lieu of radios.

In the foregoing specification, specific embodiments of the present invention have been described. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

We claim:

1. A first responder risk advisory system comprising:
   a plurality of sensors selected from the group consisting of an environment sensor and a physiological state sensor carried with a first responder, wherein said plurality of sensors produce a plurality of signals;
   a risk management signal processor coupled to said plurality of sensors, wherein said risk management signal processor is adapted to receive said plurality of signals, process said plurality of signals to deduce a level of risk to said first responder and output an indication of said level of risk;
   wherein said risk management signal processor comprises a pattern recognition engine for assigning said level of risk based on output of said plurality of sensors.

2. The first responder risk advisory system according to claim 1 wherein said plurality of sensors comprise a pulse oximeter.

3. The first responder risk advisory system according to claim 1 wherein said plurality of sensors comprise a clothing temperature sensor.

4. The first responder risk advisory system according to claim 1 wherein said plurality of sensors comprise a body temperature sensor.

5. The first responder risk advisory system according to claim 1 further comprising stored data on said first responder that is input to said risk management signal processor.

6. The first responder risk advisory system according to claim 5 wherein said stored data is selected from the group consisting of: a measure of recent work intensity, a measure of experience.

7. The first responder risk advisory system according to claim 5 further comprising a derived signal generator that generates a signal derived from said stored data and said one or more of said plurality of signals.

8. The first responder risk advisory system according to claim 5 wherein said stored data is indicative of a level of fitness of said first responder.

9. The first responder risk advisory system according to claim 8 wherein said stored data is selected from the group consisting of: resting heart rate, maximum heart rate, resting blood pressure, lung capacity, percent body fat, anaerobic threshold heart rate.

10. The first responder risk advisory system according to claim 1 wherein said first responder risk advisory system comprises an aggregator for aggregating two or more of said plurality of signals.

11. The first responder risk advisory system according to claim 10 wherein said aggregator comprises an infinite logic aggregator.

12. The first responder risk advisory system according to claim 1 wherein said plurality of sensors comprise a plurality of redundant sensors.

13. The first responder risk advisory system according to claim 12 further comprising a signal aggregator for said plurality of redundant sensors.

14. The first responder risk advisory system according to claim 13 wherein said signal aggregator comprises an infinite logic aggregator.

15. The first responder risk advisory system according to claim 14 wherein said infinite logic aggregator is configurable to perform disjunctive, conjunctive and averaging functions by setting a control parameter.

16. The first responder risk advisory system according to claim 1 wherein said plurality of sensors comprise said environment sensor and said physiological state sensor.

17. The first responder risk advisory system according to claim 1 wherein said plurality of sensors comprise a plurality of environment sensors.

18. The first responder risk advisory system according to claim 1 wherein said plurality of sensors comprise a plurality of physiological state sensors.

19. The first responder risk advisory system according to claim 18 wherein said plurality of sensors comprise a plurality of environment sensors.

20. The first responder risk advisory system according to claim 1 wherein said risk management signal processor comprises a feature vector extraction system coupled to said plurality of sensors and said pattern recognition engine and wherein said feature vector extraction system is adapted to produce feature vectors from said plurality of signals and supply said feature vectors to said pattern recognition engine.

21. The first responder risk advisory system according to claim 20 further comprising: a network adaptor for submitting said feature vectors to a remote server.

22. The first responder risk advisory system according to claim 1 wherein said risk management signal processor is carried with said first responder.

23. The first responder risk advisory system according to claim 22 wherein said one or more sensors comprise a plurality of sensors and said risk management signal processor comprises a pattern recognition engine for assigning said level of risk based on values of said plurality of sensors.

24. The first responder risk advisory system according to claim 1 wherein said plurality of sensors are coupled through a wireless channel to said a risk management signal processor.

25. The first responder risk advisory system according to claim 1 wherein said risk management signal processor is part of a commander's data terminal.

26. The first responder risk advisory system according to claim 1 wherein said risk management signal processor comprises one or more derivative filters for processing at least one of said plurality of signals.

27. The first responder risk advisory system according to claim 1 wherein said risk management signal processor comprises one or more noise removal filters for processing at least one of said plurality of signals.

28. The first responder risk advisory system according to claim 27 wherein said one or more noise removal filters comprise a Q-filter.

29. The first responder risk advisory system according to claim 1 wherein said risk management signal processor comprises one or more integrators for processing at least one of said plurality of signals.

30. The first responder risk advisory system according to claim 29 wherein said integrator is a full call duration integrator.

31. The first responder risk advisory system according to claim 1 further comprising a team risk management signal processor.

32. The first responder risk advisory system according to claim 31 wherein said team risk management signal processor receives signals from a plurality of said risk management signal processor for a plurality of first responders and outputs a team risk assessment.

33. The first responder risk advisory system according to claim 32 wherein said team risk management signal processor comprises one or more infinite logic signal aggregators for combining signals received from said plurality of said risk management signal processors for said plurality of team members.

34. The first responder risk advisory system according to claim 32 further comprising: a graphical user interface including a window that shows said team risk assessment.

35. The first responder risk advisory system according to claim 1 further comprising: a graphical user interface including a first window that shows said indication of said level of risk.

36. The first responder risk advisory system according to claim 35 wherein said graphical user interface comprises a second window that shows readouts of said plurality of sensors.

37. The first responder risk advisory system according to claim 35 wherein said graphical user interface comprises a second window that shows time series data from at least one of said plurality of sensors.

38. A first responder risk advisory system comprising: one or more servers adapted to: receive feature vectors extracted from one or more signals from one or more sensors, wherein said one or more sensors are selected from the group consisting of an environment sensor and a physiological state sensor carried with a first responder; receive information indicative of outcomes of first responder calls; and process said feature vectors and said information to determine configuration settings for a first responder risk management signal processor; and end said configuration settings to said first responder risk management signal processor.

* * * * *